US 7,479,555 B2
Jan. 20, 2009

(12) United States Patent
Alexandrov et al.

(10) Patent No.: US 7,479,555 B2
(45) Date of Patent: Jan. 20, 2009

(54) POLYNUCLEOTIDES HAVING A NUCLEOTIDE SEQUENCE THAT ENCODES A POLYPEPTIDE HAVING MOV34 FAMILY ACTIVITY

(75) Inventors: Nickolai Alexandrov, Thousand Oaks, CA (US); Vyacheslav Brover, Simi Valley, CA (US); Kenneth Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 146 days.

(21) Appl. No.: 11/180,418

(22) Filed: Jul. 13, 2005

(65) Prior Publication Data

US 2006/0037098 A1 Feb. 16, 2006

Related U.S. Application Data

(63) Continuation-in-part of application No. 11/006,231, filed on Dec. 6, 2004, which is a continuation of application No. 10/645,822, filed on Aug. 22, 2003, which is a continuation-in-part of application No. 09/513,996, filed on Feb. 25, 2000, now abandoned, and a continuation-in-part of application No. 09/620,394, filed on Jul. 21, 2000.

(60) Provisional application No. 60/145,088, filed on Jul. 21, 1999.

(51) Int. Cl.
C07H 21/04 (2006.01)
C07H 21/02 (2006.01)
C12Q 1/68 (2006.01)
C12N 1/20 (2006.01)
C12N 15/00 (2006.01)

(52) U.S. Cl. .................. 536/24.1; 435/6; 435/252.3; 435/320.1; 435/325; 536/23.1

(58) Field of Classification Search .................. None
See application file for complete search history.

(56) References Cited

U.S. PATENT DOCUMENTS

| | | | |
|---|---|---|---|
| 4,801,340 A | 1/1989 | Inoue et al. |
| 4,946,778 A | 8/1990 | Ladner et al. |
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,283,184 A | 2/1994 | Jorgensen et al. |
| 5,410,270 A | 4/1995 | Rybicki et al. |
| 5,445,934 A | 8/1995 | Fodor et al. |
| 5,538,880 A | 7/1996 | Lundquist et al. |
| 5,766,847 A | 6/1998 | Jackle et al. |
| 5,777,079 A | 7/1998 | Tsien et al. |
| 5,824,779 A | 10/1998 | Koegel et al. |
| 5,824,798 A | 10/1998 | Tallberg et al. |
| 5,900,525 A | 5/1999 | Austin-Phillips et al. |
| 5,958,745 A | 9/1999 | Gruys et al. |
| 6,013,863 A | 1/2000 | Lundquist et al. |
| 6,087,558 A | 7/2000 | Howard et al. |
| 6,136,320 A | 10/2000 | Arntzen et al. |
| 6,255,562 B1 | 7/2001 | Heyer et al. |
| 6,271,016 B1 | 8/2001 | Anderson et al. |
| 6,303,341 B1 | 10/2001 | Hiatt et al. |
| 6,326,527 B1 | 12/2001 | Kirihara et al. |
| 6,329,571 B1 | 12/2001 | Hiei |
| 6,417,429 B1 | 7/2002 | Hein et al. |
| 6,423,885 B1 | 7/2002 | Waterhouse et al. |
| 6,452,067 B1 | 9/2002 | Bedbrook et al. |
| 6,573,099 B2 | 6/2003 | Graham |
| 6,753,139 B1 | 6/2004 | Baulcombe et al. |
| 6,777,588 B2 | 8/2004 | Waterhouse et al. |
| 6,906,244 B2 | 6/2005 | Fischer et al. |
| 2003/0153097 A1 | 8/2003 | Deshaies et al. |
| 2003/0170656 A1 | 9/2003 | Cen et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2003/0229915 A1 | 12/2003 | Keddie et al. |
| 2004/0019927 A1 | 1/2004 | Sherman et al. |
| 2004/0034888 A1 | 2/2004 | Liu et al. |
| 2004/0045049 A1 | 3/2004 | Zhang et al. |
| 2004/0072159 A1 | 4/2004 | Takaiwa et al. |
| 2004/0073972 A1 | 4/2004 | Beachy et al. |
| 2004/0078852 A1 | 4/2004 | Thomashow et al. |
| 2004/0203109 A1 | 10/2004 | Lal et al. |
| 2004/0214330 A1 | 10/2004 | Waterhouse et al. |
| 2004/0216190 A1 | 10/2004 | Kovalic |
| 2006/0195934 A1 | 8/2006 | Apuya et al. |
| 2007/0199090 A1 | 8/2007 | Apuya et al. |

FOREIGN PATENT DOCUMENTS

| | | |
|---|---|---|
| EP | 1 033 405 | 9/2000 |
| EP | 6 255 72 | 4/2001 |
| WO | 95/35505 | 12/1995 |

(Continued)

OTHER PUBLICATIONS

Everett et al., Nature Genetics 17, 411-422, 1997.*

(Continued)

Primary Examiner—Shubo (Joe) Zhou
(74) Attorney, Agent, or Firm—Fish & Richardson P.C.

(57) ABSTRACT

The present invention provides DNA molecules that constitute portions of the genome of a plant. The DNA molecules are useful for expressing a gene product, either as a promoter or as a structural gene or as an UTR or as a 3' termination sequence and are also useful in controlling expression of the target gene or as tools for genetic mapping or identification of a particular individual plant or for clustering of a group of plants with a common trait.

1 Claim, No Drawings

FOREIGN PATENT DOCUMENTS

| | | |
|---|---|---|
| WO | 96/34981 | 11/1996 |
| WO | 97/01952 | 1/1997 |
| WO | 98/07842 | 2/1998 |
| WO | 98/36083 | 8/1998 |
| WO | 98/53083 | 11/1998 |
| WO | 99/24574 | 5/1999 |
| WO | 99/32619 | 7/1999 |
| WO | 99/34663 | 7/1999 |
| WO | 00/34318 | 6/2000 |
| WO | 00/34319 | 6/2000 |
| WO | 00/34320 | 6/2000 |
| WO | 00/34321 | 6/2000 |
| WO | 00/34322 | 6/2000 |
| WO | 00/34323 | 6/2000 |
| WO | 00/34324 | 6/2000 |
| WO | 00/34325 | 6/2000 |
| WO | 00/34326 | 6/2000 |
| WO | 00/55174 | 9/2000 |
| WO | 01/35725 | 5/2001 |
| WO | 02/15675 | 2/2002 |
| WO | 02/46449 | 6/2002 |
| WO | 02/055536 | 7/2002 |
| WO | 02/055669 | 7/2002 |
| WO | 03/013227 | 2/2003 |
| WO | 03/057877 | 7/2003 |
| WO | 03/060476 | 7/2003 |
| WO | 2004/004336 | 1/2004 |
| WO | 2004/039956 | 5/2004 |
| WO | 2004/041170 | 5/2004 |

OTHER PUBLICATIONS

Scott et al., Nature Genetics 21, 440-443, 1999.*
Shimanuki et al., J. Cell Sci., Feb. 1995; 108 (Pt 2): 569-79, Abstact only.*
Allen et al., Database sequence, GenBank accession No. AAY08443, Jul. 27, 1999.*
Sanches et al., JMB, vol. 370, pp. 846-855, 2007.*
Sequence alignment between Seq ID No. 2 and PSDE_ARATH, performed Mar. 1, 2007.*
U.S. Appl. No. 60/121,700, filed Feb. 25, 1999, Bouckaert et al.
GenBank Accession No. AF129516, dated Apr. 6, 1999.
GenBank Accession No. AF096096, dated Jan. 25, 1999.
GenBank Accession No. L05934, dated Oct. 22, 1993.
GenBank Accession No. AAB57606, dated May 14, 1997.
GenBank Accession No. U93215, dated Feb. 27, 2002.
GenBank Accession No. O00487, dated May 1, 2007.
GenBank Accession No. NP 005796, dated Jun. 3, 2007.
GenBank Accession No. AAC51866, dated Nov. 20, 1997.
GenBank Accession No. CAA73514, dated Jun. 12, 2006.
GenBank Accession No. O35593, dated May 1, 2007.
GenBank Accession No. NP 067501, dated Nov. 17, 2006.
GenBank Accession No. BAE29436, dated Oct. 5, 2006.
GenBank Accession No. BAE30648, dated Oct. 5, 2006.
GenBank Accession No. BAE30114, dated Oct. 5, 2006.
GenBank Accession No. BAB27974, dated Oct. 3, 2006.
GenBank Accession No. BAB27949, dated Oct. 3, 2006.
GenBank Accession No. BAA88535, dated Dec. 22, 2004.
GenBank Accession No. Q9LT08, dated May 1, 2007.
GenBank Accession No. BAA97246, dated Feb. 14, 2004.
GenBank Accession No. AAH03742, dated Jul. 15, 2006.
GenBank Accession No. NP 197745, dated Apr. 20, 2007.
GenBank Accession No. BAB78489, dated Mar. 21, 2002.
GenBank Accession No. AAL49768, dated Sep. 18, 2002.
GenBank Accession No. NP 001025636, dated Nov. 18, 2006.
GenBank Accession No. AAH97427, dated Mar. 6, 2007.
GenBank Accession No. AAH91596, dated Jul. 15, 2006.
GenBank Accession No. AAH73436, dated Aug. 3, 2004.
GenBank Accession No. AAH66336, dated Jul. 17, 2006.
GenBank Accession No. AAH45094, dated Nov. 4, 2003.
GenBank Accession No. AAM64349, dated Jan. 27, 2006.
GenBank Accession No. AAM14268, dated Sep. 18, 2002.
GenBank Accession No. AAP86672, dated Jul. 13, 2004.
GenBank Accession No. AAP86671, dated Jul. 13, 2004.
GenBank Accession No. AAP86670, dated Jul. 13, 2004.
GenBank Accession No. XP 393559, dated Jul. 26, 2006.
GenBank Accession No. AAV31238, dated Oct. 18, 2004.
GenBank Accession No. XP 515855, dated Sep. 15, 2006.
GenBank Accession No. NP 001055355, dated Oct. 3, 2006.
GenBank Accession No. NP 001042683, dated Oct. 3, 2006.
GenBank Accession No. BAF17269, dated May 19, 2007.
GenBank Accession No. BAF04597, dated Feb. 8, 2007.
GenBank Accession No. XP 535931, dated Aug. 31, 2005.
GenBank Accession No. XP 780027, dated Oct. 8, 2006.
GenBank Accession No. XP 857441, dated Aug. 31, 2005.
GenBank Accession No. ABE79516, dated Apr. 4, 2007.
GenBank Accession No. XP 001096177, dated Jun. 14, 2006.
GenBank Accession No. XP 001054967, dated Jun. 22, 2006.
GenBank Accession No. XP 001059730, dated Jun. 22, 2006.
GenBank Accession No. AAI18242, dated Jan. 23, 2007.
GenBank Accession No. BAF00543, dated Jul. 27, 2006.
GenBank Accession No. NP 001069535, dated Nov. 18, 2006.
GenBank Accession No. XP 001177147, dated Oct. 9, 2006.
Office Action from U.S. Appl. No. 11/153,185, document dated Dec. 28, 2006, 5 pages; Mar. 28, 2007 Response to Office Action dated Dec. 28, 2006, 16 pages; Notice of Allowance from U.S. Appl. No. 11/153,185, dated Jun. 19, 2007.
Office Action from U.S. Appl. No. 11/180,101, document dated Dec. 28, 2006, 5 pages; Mar. 28, 2007 Response to Office Action dated Dec. 28, 2006, 15 pages; Notice of Allowance from U.S. Appl. No. 11/180,101, dated Jun. 19, 2007.
Office Action from U.S. Appl. No. 11/362,437, document dated Apr. 9, 2007, 24 pages; Jul. 9, 2007 Response to Office Action dated Apr. 9, 2007, 7 pages; Notice of Allowance from U.S. Appl. No. 11/362,437, dated Aug. 9, 2007.
Office Action from U.S. Appl. No. 11/358,685, document dated Apr. 5, 2007, 15 pages; Aug. 3, 2007 Response to Office Action dated Apr. 5, 2007, 7 pages.
Office Action from U.S. Appl. No. 11/357,909, document dated Apr. 9, 2007, 10 pages; Jul. 9, 2007 Response to Office Action dated Apr. 9, 2007, 6 pages.
Office Action from U.S. Appl. No. 11/357,747, document dated Apr. 9, 2007, 27 pages; Aug. 3, 2007 Response to Office Action dated Apr. 9, 2007, 8 pages.
Office Action from U.S. Appl. No. 11/362,546, document dated Nov. 15, 2006, 6 pages; Feb. 14, 2007 Response to Office Action dated Nov. 15, 2006, 7 pages.
Office Action from U.S. Appl. No. 11/362,546, document dated May 2, 2007, 6 pages; Jul. 2, 2007 Response to Office Action dated May 2, 2007, 4 pages.
Office Action from U.S. Appl. No. 11/368,322, document dated Apr. 4, 2007, 25 pages.
Office Action from U.S. Appl. No. 11/367,760, document dated Apr. 10, 2007, 26 pages; Jul. 10, 2007 Response to Office Action dated Apr. 10, 2007, 10 pages.
Office Action from U.S. Appl. No. 11/368,321, document dated Aug. 29, 2007, 9 pages.
Office Action from U.S. Appl. No. 11/369,193, document dated Nov. 15, 2006, 7 pages; Feb. 14, 2007 Response to Office Action dated Nov. 15, 2006, 5 pages.
Office Action from U.S. Appl. No. 11/369,173, document dated Nov. 15, 2006, 14 pages; Feb. 14, 2007 Response to Office Action dated Nov. 15, 2006, 8 pages.
Office Action from U.S. Appl. No. 11/369,173, document dated May 3, 2007, 15 pages.
Office Action from U.S. Appl. No. 11/372,369, document dated Apr. 5, 2007, 18 pages; Jul. 5, 2007 Response to Office Action dated Apr. 5, 2007, 7 pages; Notice of Allowance from U.S. Appl. No. 11/372,369, dated Aug. 23, 2007.
Office Action from U.S. Appl. No. 11/396,378, document dated May 2, 2007, 14 pages; Aug. 2, 2007 Response to Office Action dated May 2, 2007, 4 pages.

Office Action from U.S. Appl. No. 11/396,457, document dated May 7, 2007, 11 pages; Jul. 2, 2007 Response to Office Action dated May 2, 2007, 4 pages.

Abler et al. "Isolation and characterization of a genomic sequence encoding the maize Cat3 catalase gene" *Plant Mol. Biol.*, 22:10131-1038 (1993).

Ahn et al., "Homoeologous relationships of rice, wheat and maize chromosomes" *Molecular and General Genetics*, 241:483-90 (1993).

Allen et al. "RNAi-mediated replacement of morphine with the non-narcotic alkaloid reticuline in opium poppy" *Nature Biotechnology*, 22(12):1559-1566 (2004).

Alonso-Blanco et al., Methods in Molecular Biology, vol. 82, "Arabidopsis Protocols", pp. 137-146, J.M. Martinez-Zapater and J. Salinas, eds., c. 1998 by *Human Press*, Totowa, NJ.

Aravind, "Homologues of 26S proteasome subunits are regulators of transcription and translation" *Protein Science*, 7:1250-1254 (1998).

Armaleo et al., "Biolistic nuclear transformation of *Saccharomyces cerevisiae* and other fungi" *Current Genetics*, 17:97 (1990).

Ausubel et al. 1992 (Current Protocols in Molecular Biology, Greene Publishing, New York).

Azpiroz-Leehan et al., "T-DNA insertion mutagenesis in *Arabidopsis*: going back and forth" *Trends in Genetics*, 13:152 (1997).

Baerson et al., "Development regulation of an acyl carrier protein gene promotor in vegetative and reproductive tissues" *Plant Mol. Biol.*, 22(2):255-267 (1993).

Bateman et al., "Pfam 3.1: 1313 multiple alignments and profile HMMs match the majority of proteins" *Nucl. Acids Res.*, 27:260-262 (1999).

BD Matchmaker One-Hybrid Library construction & Screening Kit, *Clonetechniques*, 2003.

Bechtold et al., "In planta *Agrobacterium* mediated gene transfer by infiltration of adult *Arabidopsis thaliana* plants" *C.R. Acad. Sci. Paris*, 316:1194-1199 (1993).

Bird et al. "A tale of three cell types: alkaloid biosynthesis is localized to sieve elements in opium poppy" *The Plant Cell*, 15:2626-2635 (2003).

Biswas et al. "Transgenic indica rice (*Oryza sativa* L.) plants obtained by direct gene transfer to protoplasts" *J. Biotechnol.* 32:1 (1994).

Blattner et al., "The complete genome sequence of *Escherichia coli* K-12" *Science* 277:1453 (1997).

Bonner et al., "Reduction in the rate of DNA reassociation by sequence divergence" *J. Mol. Biol.*, 81:123 (1973).

Burr ("Mapping Genes with Recombinant Inbreds", pp. 249-254. In Freeling, M. and V. Walbot (Ed.), The Maize Handbook, c. 1994 by Springer-Verlag New York, Inc.: New York, NY, USA; Berlin Germany.

Burr et al., "Gene mapping with recombinant inbreds in maize" *Genetics*, 118:519 (1998).

Busk et al. "Regulatory elements in vivo in the promoter of the abscisic acid responsive gene *rab17* from maize" *Plant Journal*, 11:1285-1295 (1997).

Bustos et al., "Regulation of β-Glucuronidase expression in transgenic tobacco plants by an A/T-rich, *cis*-Acting sequence found upstream of a French bean β-Phaseolin gene" *The Plant Cell*, 1:839-854 (1989).

Oeller et al., "Reversible inhibition of tomato fruit senescence by antisense RNA" *Science*, 254:437-439 (1991).

Ounaroon et al. "(R, S)-Reticuline 7-O-methyltrasnferase and (R, S)-norcoclaurine 6-O-methyltransferase of *Papaver somniferum*—cDNA cloning and characterization of methyl transfer enzymes of alkaloid biosynthesis in opium poppy" *The Plant Journal* (2003).

Panaud et al., "Frequency of microsatellite sequences in rice (*Oryza sative* L.)" *Genome*, 38:1170 (1995).

Park et al., "Agrobacterium rhizogenes-mediated transformation of opium poppy, *Papaver somniferum* L., and California poppy, *Eschscholzia californica* Cham., root cultures" *J. Exp. Botany*, 2000, 51(347):1005-1016.

Park & Facchini, "High-efficiency somatic embryogenesis and plant regeneration in California poppy, *Eschscholzi califronica* Cham." *Plant Cell Rep* 19: 421-426, (1999).

Park & Facchini, "*Agrobacterium*-mediated genetic transformation of California poppy, *Eschscholzia californica* Cham., via somatic embryogenesis" *Plant Cell Reports*, 19:1006-1012 (2000).

Paszkowski et al. "Direct gene transfer to plants" *EMBO J.*, 3:2717 (1984).

Pearson and Lipman "Improved tools for biological sequence comparison" *Proc. Natl. Acad. Sci. USA*, 85: 2444 (1988).

Perriman et al., "Effective ribozyme delivery in plant cells" *Proc. Natl. Acad. Sci. USA*, 92(13):6175-6179 (1995).

Refseth et al., "Hybridization capture of microsatellites directly from genomic DNA" *Electrophoresis*, 18:1519 (1997).

Riechmann et al. "*Arabidopsis* transcription factors: genome-wide comparative analysis among eukaryotes" *Science*, 290:2105-2110 (2000).

Riggs et al., "Cotyledon nuclear proteins bind to DNA fragments harboring regulatory elements of phytohemagglutinin genes" *Plant Cell*, 1(6):609-621 (1989).

Rivera et al, "Genomic evidence for two functionally distinct gene classes" *Proc. Natl. Acad. Sci. USA* ,1998, 95:6239-6244.

Rogers, S. G. et al., "Gene transfer in plants: production of transformed plans using ti plasmid vectors" *Methods in Enzymology*, 118:627 (1986).

Roulet et al., "Evaluation of computer tools for the prediction of transcription factor binding sites on genomic DNA" obtained from the internet on Aug. 6, 2004 at http://www.bioinfo.de/isb/1998/01/0004/main.html, 7 pages.

Salomon et al., "Genetic identification of functions of TR-DNA transcripts in octopine crown galls" *EMBO J.*, 3:141 (1984).

Sambrook et al., 1989, "Molecular Cloning, A Laboratory Manual", second edition, *Cold Spring Harbor Press*, Plainview; NY.

Senoir et al., "Simple sequence repeat markers developed from Maize sequences found in the Genbank database: Map construction" *Crop Science*, 36:1676 (1996).

Seki et al., "High-efficiency cloning of *Arabidopsis* full-length cDNA by biotinylated CAP trapper" *Plant Journal*, 15(5): 707-720 (1998).

Sheehy et al., "Reduction of polygalacturonase activity in tomato fruit by antisense RNA" *Proc. Nat. Acad. Sci. USA*, 85:8805 (1988).

Sheridan, "The *mac1* Gene: Controlling the commitment to the meiotic pathway in Maize" *Genetics*, 1996, 142:1009-1020.

Slocombe et al., "Temporal and tissue-specific regulation of a *Brassica napus* stearoyl-acyl carrier protein desaturase gene" *Plant Physiol.*, 1994, 104(4):167-176.

Smith and Waterman, "Comparison of Biosequences" *Advances in Applied Mathematics.*, 2:482 (1981).

Sonnhammer et al., "Pfam: A comprehensive database of protein domain families based on seed alignments" *Proteins*, 28:405-420 (1997).

Sonnhammer et al., "Pfam: multiple sequence alignments and HMM-profiles of protein domains" *Nucl. Acids Res.*, 26:320-322 (1998).

Summerton and Weller, "Morpholino antisense oligomers: design, preparation, and properties" *Antisense Nucleic Acid Drug Dev.*, 7:187-195 (1997).

Taramino et al., "Simple sequence repeats for germplasm analysis and mapping in maize" *Genome*, 39:277 (1996).

Tijessen, "Hybridization with Nucleic Acid Probes" in Laboratory Techniques in Biochemistry and Molecular Biology, P.C. van der Vliet, ed., c. 1993 by *Elservier*, Amsterdam.

Truernit et al., "The promoter of the *Arabidopsis thaliana* SUC2 sucrose-H$^+$ symporter gene directs expression of β-glucuronidase to the phloem: Evidence for phloem loading and unloading by SUC2" *Planta*. 196:564-570 (1995).

Urao et al. "Molecular cloning and characterization of a gene that encodes a MYC-related protein in *Arabidopsis*" *Plant Mol. Biol.*, 32:571-57 (1996).

Urdea et al. "Chemical synthesis of a gene for human epidermal growth factor urogastrone and its expression in yeast" *Proc. Natl. Acad. Sci. USA*, 80:77461 (1983).

van der Krol et al., "Flavonoid genes in petunia: Addition of a limited number of gene copies my lead to a suppression of gene expression" *The Plant Cell*, 2:291 (1990).

Venkateswarlu et al., "Evidence for T-DNA mediated gene targeting to tobacco chloroplasts" *Biotechnology*, 9:1103 (1991).

Vergunst et al., "Site-specific integration of *Agrobacterium* T-DNA in *Arabidopsis thaliana* mediated by Cre recombinase" *Nucleic Acids Res.*, 26:2729 (1998).

Verpoorte et al. "Engineering secondary metabolite production in plants" *Current Opinion in Biotechnology*, 13(2):181-187 (2002).

Weising et al., "Foreign genes in plants: transfer, structure, expression, and applications" *Ann. Rev. Genet.*, 22:421 (1988).

Weiss, "Hot prospect for new gene amplifier" *Science*, 254:1292 (1991).

Williams et al., "Development of a PCR-based allele-specific assay from an FRLP probe linked to resistance to cereal cyst nematode in wheat" Genome 39:7, 798 (1996).

Wroblewski et al. "Optimization of *Agrobacterium*-mediated transient assays of gene expression in lettuce, tomato and *Arabidopsis*" *Plant Biotechnology Journal*, 3:259-273 (2005).

Xiong et al. "Repression of stress-responsive genes by FIERY2, a novel transcriptional regulator in *Arabidopsis*" *Proc. Natl. Acad. Sci. USA*, 99(16)10899-10904 (2002).

Xu et al., "Characterization of a rice gene family encoding root-specific proteins" *Plant Molecular Biology*. 27:237 (1995).

Yamamoto et al., "Characterization of *cis*-Acting sequences regulating root-specific gene expression in tobacco" *Plant Cell*, 3:371 (1991).

Yamamoto et al., "The promoter of a pine photosynthetic gene allows expression of a β-glucuronidase reporter gene in transgenic rice plants in a light-independent but tissue-specific manner" *Plant Cell Physiol.*, 1994 35:773-778.

Yanagisawa "Transcription factors in plants: physiological functions and regulation of expression" *J. Plant Res.*, 111:363-371 (1998).

Zhang, et al., "DNA sequences that activate Isocitrate Lyase gene expression during late embryogenesis and during postgerminative growth" *Plant Physiology*, 1996, 110: 1069-1079.

Zhang et al. "Metabolic engineering of tropane alkaloid biosynthesis in plants" *Journal of Integrative Plant Biology*, 47(2):136-143 (2005).

Zheng et al., "*SPK1* Is an Essential S-Phase-Specific Gene of *Saccharomyces cerevisiae* that encodes a nuclear serine/threonine/tyrosine kinase" *Mol. Cell Biol.*, 1993, 13:5829-5842.

Office Action from U.S. Appl. No. 11/370,240, dated Sep. 27, 2007, 8 pages.

Final Office Action from U.S. Appl. No. 11/357,357, dated Nov. 29, 2007, 9 pages.

Office Action from U.S. Appl. No. 11/370,253, dated Oct. 30, 2007, 20 pages.

Office Action from U.S. Appl. No. 11/371,356, dated Oct. 30, 2007, 20 pages.

Office Action from U.S. Appl. No. 11/371,624, dated Oct. 31, 2007, 21 pages.

Office Action from U.S. Appl. No. 11/396,357, dated Nov. 7, 2007, 7 pages.

Office Action from U.S. Appl. No. 11/371,623, dated Nov. 16, 2007, 10 pages.

Office Action from U.S. Appl. No. 11/369,168, dated Oct. 30, 2007, 20 pages.

Notice of Allowance from U.S. Appl. No. 11/367,760, dated Oct. 5, 2007, 6 pages.

Notice of Allowance from U.S. Appl. No. 11/153,185, dated Nov. 13, 2007, 7 pages.

Notice of Allowance from U.S. Appl. No. 11/372,369, dated Nov. 13, 2007, 7 pages.

Notice of Allowance from U.S. Appl. No. 11/396,378, dated Nov. 13, 2007, 7 pages.

Response to Office Action from U.S. Appl. No. 11/368,321, filed Nov. 29, 2007, 5 pages.

Carels et al., "Compositional properties of homologous coding sequences from plants" *J. Mol. Evol.*, 46:45 (1998).

Casaretto et al. "The transcription factors HvABI5 and HvVP1 are required for the abscisic acid induction of gene expression in barley aleuron cells" *The Plant Cell*, 15:271-284 (2003).

Cerdan et al., "A 146 bp fragment of the tobacco *Lhcb1\*2* promoter confers very-low-fluence, low-fluence and high-irradiance responses of phytochrom to a minimal CaMV 35S promoter" *Plant Mol. Biol.*, 33:245-255 (1997).

Chang et al., "The Exo-gap method employing the phage f1 endonuclease generates a nested set of unidirectional deletions" *Gene*, 127:95 (1993).

Chen et al., "Functional analysis of regulatory elements in a plant embryo-specific gene" *Proc. Natl. Acad. Sci. USA*, 83:8560-8564 (1986).

Chen et al. "Expression profile matrix of arabidopsis transcription factor genes suggests their putative functions in response to environmental stresses" *The Plant Cell*, 14:559-574 (2002).

Chenna et al., "Multiple sequence alignment with the Clustal series of programs" *Nucleic Acids Res.*, 31(13):3497-500 (2003).

Chinnusamy et al. "Screening for gene regulation mutants by bioluminescence imaging" Obtained from the internet at www.stke.org/cgi/content/full/sigtrans;2002/140/p110, Jul. 9, 2002.

Chitty et al., "Genetic transformation in commercial Tasmanian cultures of opium poppy, Papaver somniferum, and movement of transgenic pollen in the field," *Funct. Plant Biol*. 30:1045-1058 (2003).

Chou et al. "Enzymatic oxidation in the biosynthesis of complex alkaloids" *The Plant Journal*, 15(3):289-300 (1998).

Christou, "Strategies for variety-independent genetic transformation of important cereals, legumes and woody species utilizing particle bombardment" *Euphytica*, 85(1-3):13-27, (1995).

Conceicao, "A cotyledon regulatory region is responsible for the different spatial expression patterns of *Arabidopsis* 2S albumin genes" *The Plant Jour.*, 1994, 5(4):493-505.

Conkling et al. "Isolation of transcriptionally regulated root-specific genes from tobacco" *Plant Physiol.*, 1990, 93:1203-1211.

Cormack et al. "Leucine zipper-containing WRKY proteins widen the spectrum of immediate early elicitor-induced WRKY transcription factors in parsley" *Biochimica et Biophysica Acta*, 1572:92-100 (2002).

Cox et al., "Plant Molecular Biology: A Practical Approach", pp. 1-35, Shaw ed., c. 1988 by IRL, Oxford.

Dai et al., "RF2b, a rice bZIP transcription activator, interacts with RF2a and is involved in symptom development of rice tungro disease" *Proc. Natl. Acad. Sci. USA*, 101(2):687-692 (2004).

de Feyter and Gaudron, Methods in Molecular Biology, vol. 74, Chapter 43, "Expressing Ribozymes in Plants", Edited by Turner, P.C., *Humana Press Inc.*, Totowa, NJ, 1997.

Dr. Duke's Phytochemical and ethnobotanical databases, obtained from the Internet on Feb. 9, 2005 at http://www.ars-grin.gov/cgi-bin/duke/farmacy2.pl, 7 pages.

Elegans et al. "Genome sequence of the nematode C. elegans: a platform for investigating biology" *Science* 282:2012 (1998).

Escudero et al., "T-DNA transfer in meristematic cells of maize provided with intracellular *Agrobacterium*" *Plant J.*, 10:355 (1996).

Evans et al., Protoplasts Isolation and Culture in."Handbook of Plant Cell Culture," pp. 124 176, *MacMillilan Publishing Company*, New York, 1983.

Facchini "Alkaloid biosynthesis in plants: Biochemistry, cell biology, molecular regulation, and metabolic engineering applications" *Annu. Rev. Plant Physiol. Plant Mol. Biol.* 52:29-66 (2001).

Fejes et al., "A 268 bp upstream sequence mediates the circadian clock-regulated transcription of the wheat Cab-1 gene in transgenic plants" *Plant Mol. Biol.*, 15:921-932 (1990).

Fennoy et al. "Synonymous codon usage in *Zea mays* L. nuclear genes is varied by levels of C and G-ending codons" *Nucleic Acids Research*, 21(23):5294 (1993).

Fromm et al. "Expression of genes transferred into monocot and dicot plant cells by electroporation" *Proc. Natl. Acad. Sci. USA*, 82:5824 (1985).

Fromm et al., "An octopine synthase enhancer element directs tissue-specific expression and binds ASF-1, a factor from tobacco nuclear extracts" *The Plant Cell*, 1:977-984 (1989).

Fry et al., "A new approach to template purification for sequencing applications using paramagnetic particles" *Biotechniques*, 13: 124 (1992).

Gardiner et al., "Development of a core RFLP map in maize using an immortalized F2 population" *Genetics*, 134:917 (1993).

Gleave, AP., "A versatile binary vector system with a T-DNA organizational structure conductive to efficient integration of cloned DNA into the plant genome" *Plant Mol. Biol.*, 20:1203 (1992).

Gofieau et al., "Life with 6000 genes" *Science*, 274:546 (1996).

Gould et al., "Transformation of *Zea mays* L. Using *Agrobacterium tummefaciens* and the shoot apex" *Plant Physiology*, 95:426 (1991).

Graves and Goldman, "The transformation of *Zea mays* seedling with *Agrobacterium tumefaciens*" *Plant Mol. Biol.*, 7:34 (1986).

Green et al., "Binding site requirements for pea nuclear protein factor GT-1 correlate with sequences required for light-dependent transcriptional activation of the *rbcS-3A* gene" *EMBO J.*, 7:4035-4044 (1988).

Guatelli et al., "Isothermal, in vitro amplification of nucleic acids by a multienzyme reaction modeled after retroviral replication" *Proc. Natl. Acad. Sci. USA*, 87:1874-1878 (1990).

Guilfoyle, "Ligation-mediated PCR amplification of specific fragments from a class-II restriction endonuclease total digest" *Nucleic Acids Res.*, 25:9, 1854 (1997).

Hamilton, "A binary-BAC system for plant transformation with high-molecular-weight DNA" *Gene*, 200:107-116 (1997).

Haseloff et al. "Simple RNA enzymes with new and highly specific endoribonuclease activities" *Nature*, 334:585 (1988).

Hellens et al. "Transient expressions vectors for functional genomics, quantification of promotor activity and RNA silencing in plants" *Plant Methods*, 1:13 (2005).

Herrera-Estrella et al., "Chimeric genes as dominant selectable markers in plant cells" *EMBO J.*, 2:987 (1983).

Hershey et al., "Conservation and diversity in the structure of translation initiation factor eIF3 from humans and yeast" *Biochemie*, 78:903-907, 1996.

Hilbricht et al. "CpR18, a novel SAP-domain plant transcription factor, binds to a promoter region necessary for ABA mediated expression of the *CDeT27-45* gene from the resurrection plant *Craterostigma plantagineum* Hochst" *The Plant Journal*, 31(3):293-303 (2002).

Hong et al., "Promoter sequences from two different *Brassica napus* tapetal oleosin-like genes direct tapetal expression of β-glucuronidase in transgenic *Brassica* plants" *Plant Mol Biol.*, 1997 34(3):549-555.

Hosoyama et al. "Oryzacystatin exogenously introduced into protoplasts and regeneration of transgenic rice" *Biosci. Biotechnol. Biochem.*, 58(8):1500-1505 (1994).

Hwang and Goodman, "An *Arabidopsis thaliana* root-specific kinase homolog is induced by dehydration, ABA, and NaCl" *Plant J.* 8:37 (1995).

Hyrup et al., Peptide nucleic acids (PNA): synthesis, properties and potential applications *Bioorgan. Med. Chem.*, 4:5-23 (1996).

Ishida et al., "High efficiency transformation of maize (*Zea mays* L. mediated by *Agrobacterium tumefaciens*" *Nature Biotechnology*, 14:745 (1996).

Jakoby et al., "bZIP transcription factors in *Arabidopsis*" *Trends in Plant Science*, 7(3):106-111 (2002).

Joh et al. "High-level transient expression of recombinant protein in lettuce" *Biotechnology and Bioengineering*, 91(7):861-871 (2005).

Jordano et al., "A sunflower helianthinin gene upstream sequence ensemble contains an enhancer and sites of nuclear protein interaction" *Plant Cell*, 1:855-866 (1989).

Kato et al., "Construction of a human full-length cDNA bank" *Gene* 150:243-250 (1994).

Keller and Baumgartner, "Vascular-specific expression of the bean GRP 1.8 gene is negatively regulated" *Plant Cell*, 3(10):1051-1061 (1991).

Keller and Manak "DNA Probes", 2nd Ed. pp. 1-25, c. 1993 by *Stockton Press*, New York, NY.

Kim et al. "A novel cold-inducible zinc finger protein from soybean, SCOF-1, enhances cold tolerance in transgenic plants" *The Plant Journal*, 25(3):247-259 (2001).

Kim et al. "Arabidopsis ABI5 subfamily members have distinct DNA-binding and transcriptional activities" *Plant Physiology*, 130:688-697 (2002).

Kizis et al. "Maize DRE-binding proteins DBF1 and DBF2 are involved in *rab17* regulation through the drought-responsive element in an ABA-dependent pathway" *The Plant Journal*, 30(6):679-689 (2002).

Klein et al., "High-velocity microprojectiles for delivering nucleic acids into living cells" *Nature*, 327:773 (1987).

Kohler and Milstein "Continuous cultures of fused cells secreting antibody of predefined specificity" *Nature*, 256: 495 (1975).

Koltonow et al., "Different temporal and spatial gene expression patterns occur during anther development" *Plant Cell*, 2:1201 (1990).

Komari et al., "Vectors carrying two separate T-DNAs for co-transformation of higher plants mediated by *Agrobacterium tumefaciens* and segregation of transformants free from selection markers" *Plant J.*, 10:165 (1996).

Kuhlmann et al. "The a-Helical D1 domain of the tobacco bZIP transcription factor BZI-1 interacts with the ankyrin-repeat protein ANK1 and is important for BZI-1 function, both in auxin signaling and pathogen response" *The Journal of Biological Chemistry*, 278(10) 8786-8794 (2003).

Kutchan "Molecular genetics of plant alkaloid biosynthesis" *The Alkaloids*, 50:257-316, 1998.

Lam et al., "Site-specific mutations in alter in vitro factor binding and change promoter expression pattern in transgenic plants" *Proc. Natl. Acad. Sci. USA*, 86:7890-7894 (1989).

Lewis, *Genetic Engineering News*, 12(9):1 (1992).

Li et al., "Generation of destabilized green fluorescent protein as a transcription reporter" *J. Biol. Chem.* 1998, 273:34970-5.

Liu et al. "Two transcription factors, DREB1 and DREB2, with an EREBP/AP2 binding domain separate two cellular signal transduction pathways in drought- and low- temperature-responsive gene expression , respectively, and Arabidopsis" *The Plant Cell*, 10:1391-1406 (1998).

Lu et al. "Three novel MYB proteins with one DNA binding repeat mediate sugar and hormone regulation of a-amylase gene expression" *The Plant Cell*, 14:1963-1980 (2002).

Luan et al., "A rice *cab* gene promoter contains separate *cis*-acting elements that regulate expression in dicot and monocot plants" *The Plant Cell*, 1992, 4:971-981.

Lubberstedt et al., "Promoters from genes for plastid proteins possess regions with different sensitivities toward red and blue light" *Plant Physiol.*, 104:997-1006 (1994).

Mariani et al., "A chimeric ribonuclease-inhibitor gene restores fertility to male sterile plants" *Nature*, 357: 384-387 (1992).

Mariconti et al. "The E2F family of transcription factors from *Arabidopsis thaliana*" *The Journal of Biological Chemistry*, 277(12):9911-9919 (2002).

Matsuoka et al., "Tissue-specific light-regulated expression directed by the promoter of a C4 gene, maize pyruvate, orthophosphate dikinase, in a C3 plant, rice" *Proc. Natl. Acad. Sci. USA*, 90:9586-9590 (1993).

Maruyama et al., "Oligo-capping: a simple method to replace the cap structure of eukaryotic mRNAs with oligoribonucleotides" *Gene*, 138:171 (1994).

Matteucci et al. "Synthesis of Deoxyoligonucleotides on a polymer support" *J. Am. Chem. Soc.*, 103:3185 (1981).

May et al., "Generation of transgenic banana (*Musa acuminate*) plants via *Agrobacterium*-mediated transformation" *Bio/Technology*, 13:486 (1995).

McCormac et al., "A flexible series of binary vectors for agrobacterium-mediated plant transformation" *Mol. Biotechnol.*, 8:199 (1997).

Medberry et al., "The Commelina yellow mottle virus promoter is a strong promoter in vascular and reproductive tissues" *Plant Cell*, 4(2):185-192 (1992).

Meier et al, "Elicitor-inducible and constitutive in vivo DNA footprints indicate novel *cis*-acting elements in the promoter of a parsley gene encoding pathogenesis-related protein 1" *Plant Cell*, 3:309-316 (1991).

Memelink "Putting the opium in poppy to sleep" *Nature Biotechnology*, 22(12):1526-1527, 2004.

Müller et al., "High meiotic stability of a foreign gene introduced into tobacco by *Agrobacterium*-mediated transformation" *Mol. Gen. Genet.*, 207:171 (1987).

Napoli et al., "Introduction of a chimeric chalcone synthase gene into petunia results in reversible co-suppression of homologous genes in trans." *The Plant Cell*, 2:279 (1990).

Needleman and Wunsch "A general method applicable to the search for similarities in the amino acid sequence of two proteins" *J. Mol. Biol.*, 48:443 (1970).

Notice of Allowance from U.S. Appl. No. 11/180,101, dated Apr. 28, 2008, 7 pages.

Response to Final Office Action from U.S. Appl. No. 11/357,357, filed Apr. 29, 2008, 5 pages; and Advisory Action, dated May 14, 2008, 3 pages.

Notice of Allowance from U.S. Appl. No. 11/362,437, dated Apr. 28, 2008, 7 pages.

Office Action from U.S. Appl. No. 11/368,323, dated Mar. 24, 2008, 8 pages.

Office Action from U.S. Appl. No. 11/388,215, dated Apr. 3, 2008, 7 pages.

Final Office Action from U.S. Appl. No. 11/369,168, dated Apr. 16, 2008, 9 pages.

Final Office Action from U.S. Appl. No. 11/370,253, dated May 16, 2008, 9 pages.

Final Office Action from U.S. Appl. No. 11/371,356, dated Apr. 17, 2008, 9 pages.

Final Office Action from U.S. Appl. No. 11/371,624, dated Apr. 16, 2008, 9 pages.

Notice of Allowance from U.S. Appl. No. 11/371,623, dated May 29, 2008, 8 pages.

Office Action from U.S. Appl. No. 11/387,751, dated May 23, 2008, 10 pages.

Notice of Allowance from U.S. Appl. No. 11/358,685, dated Dec. 21, 2007, 4 pages.

Notice of Allowance from U.S. Appl. No. 11/357,747, dated Dec. 21, 2007, 4 pages.

Notice of Allowance from U.S. Appl. No. 11/357,909, dated Dec. 21, 2007, 4 pages.

Notice of Allowance from U.S. Appl. No. 11/368,321, dated Dec. 21, 2007, 4 pages.

Notice of Allowance from U.S. Appl. No. 11/362,546, dated Jan. 23, 2008, 6 pages.

Notice of Allowance from U.S. Appl. No. 11/357,760, dated Feb. 28, 2008, 4 pages.

Response to Office Action from U.S. Appl. No. 11/369,168, filed Jan. 30, 2008, 7 pages.

Response to Office Action from U.S. Appl. No. 11/370,253, filed Jan. 30, 2008, 7 pages.

Response to Office Action from U.S. Appl. No. 11/371,356, filed Jan. 30, 2008, 7 pages.

Response to Office Action from U.S. Appl. No. 11/371,624, filed Jan. 30, 2008, 8 pages.

Response to Office Action from U.S. Appl. No. 11/371,623, filed Feb. 15, 2008, 4 pages.

\* cited by examiner

POLYNUCLEOTIDES HAVING A NUCLEOTIDE SEQUENCE THAT ENCODES A POLYPEPTIDE HAVING MOV34 FAMILY ACTIVITY

RELATED-APPLICATIONS

This application is a continuation-in-part of U.S. patent application Ser. No. 11/006,231 filed Dec. 6, 2004, which is a continuation of U.S. patent application Ser. No. 10/645,822 filed Aug. 22, 2003, which is (1) a continuation-in-part of U.S. patent application Ser. No. 09/513,996 filed on Feb. 25, 2000 now abandoned, which claims the benefit of priority to U.S. Provisional Patent Application No. 60/145,088, filed Jul. 21, 1999, and (2) a continuation-in-part of U.S. patent application Ser. No. 09/620,394 filed on Jul, 21, 2000, which claims the benefit of priority to U.S. Provisional Patent Application No. 60/145,088, filed Jul. 21, 1999. The entire contents of these related applications are incorporated by reference in their entirety.

BACKGROUND

1. Technical Field

The present invention relates to isolated polynucleotides that encode all, or a portion of, a gene that is expressed and the corresponding polypeptide. The present invention also relates to isolated polynucleotides that encode regulatory regions of genes.

2. Background Information

Efforts to map and sequence the genome of a number of organisms are in progress; a few complete genome sequences, for example those of *E. coli* and *Saccharomyces cerevisiae* are known (Blattner et al., *Science* 277:1453 (1997); Goffeau et al., *Science* 274:546 (1996)). The complete genome of a multicellular organism *C. elegans* has also been sequenced (See, the *C. elegans* Sequencing Consortium, Science 282: 2012 (1998)). To date, no complete genome of a plant has been sequenced, nor has a complete cDNA complement of any plant been sequenced.

SUMMARY

The present invention comprises polynucleotides, such as cDNA sequences and/or genomic fragments, hereinafter collectively referred to as "Sequence-Determined DNA Fragments" (SDFs), from *Zea mays* or *Arabidopsis thaliana* and polypeptides derived therefrom. In some instances, the SDFs span the entirety of a protein-coding segment. In some instances, the entirety of an mRNA is represented. Other objects of the invention are the control sequences such as, but not limited to, promoters that are also represented by SDFs of the invention.

Other objects of the invention are polynucleotides comprising intron sequences, polynucleotides comprising introns together with exons, intron/exon junction sequences, 5' untranslated sequences, and 3' untranslated sequences of the SDFs of the present invention.

The present invention also resides in probes useful for isolating and identifying nucleic acids that hybridize to an SDF of the invention. The probes are typically of a length of 12 to 2000 nucleotides long; more typically, 15 to 200 nucleotides long; even more typically, 18 to 100 nucleotides long.

Yet another object of the invention is a method of isolating and/or identifying nucleic acids using the following steps:

(a) contacting a probe of the instant invention with a polynucleotide sample under conditions that permit hybridization and formation of the polynucleotide duplex; and (b) detecting and/or isolating the duplex of step (a).

The conditions for hybridization can be from low to moderate to high stringency conditions. The sample can include a polynucletoide having a sequence unique in a plant genome. Probes and methods of the invention are useful, for example, without limitation, for mapping of genetic traits and/or for positional cloning of a desired portion of genomic DNA. Probes and methods of the invention can also be used for detecting related genes in other plant species in genomic DNA (gDNA) and/or cDNA libraries. In some instances, especially when longer probes and low to moderate stringency hybridization conditions are used, the probe will hybridize to a plurality of cDNA and/or gDNA sequences of a plant. This approach is useful for isolating representatives of gene families which are identifiable by possession of a common functional domain in the gene product or which have common cis-acting regulatory sequences. This approach is also useful for identifying orthologous genes from other organisms, which can be more or less related to corn or *Arabidopsis*.

The present invention also resides in constructs for modulating the expression of the genes comprised of all or a portion of an SDF. The constructs comprise all or a portion of the expressed SDF, or of a complementary sequence. Examples of constructs include ribozymes comprising RNA encoded by an SDF or by a sequence complementary thereto, antisense constructs, constructs comprising coding regions or parts thereof, constructs comprising promoters, introns, untranslated regions, etc. When inserted into a host cell the construct is preferably functionally integrated with or operatively linked to a heterologous polynucleotide. For instance, a coding region from an SDF might be operably linked to a promoter that is functional in a plant.

The present invention also resides in host cells, including bacterial or yeast cells or plant cells, and transgenic plants that harbor constructs such as described above. Another aspect of the invention relates to methods for modulating expression of specific genes in transgenic plants by expression of the structural gene component of the constructs, by regulation of expression of one or more endogenous genes in a transgenic plant or by suppression of expression of the polynucleotides of the invention in a transgenic plant. Methods of modulation include without limitation (1) inserting into a host cell additional copies of a polynucleotide comprising a coding sequence; (2) modulating an endogenous promoter in a host cell; (3) inserting antisense or ribozyme constructs into a host cell and (4) inserting into a host cell a polynucleotide comprising a sequence encoding a mutant, fragment, or fusion of the native polypeptides of the instant invention.

BRIEF DESCRIPTION OF THE TABLES

The SDFs of the instant invention are listed in Table 2; annotations relevant to the sequences shown in Table 2 are presented in Table 1. Each sequence corresponds to a clone number. Each clone number corresponds to at least one sequence in Table 2.

Table 1 is a Reference Table which correlates each of the sequences and SEQ ID NOs in Table 2 with a corresponding Ceres clone number, Ceres sequence identifier, and other information about the individual sequence. Table 2 is a Sequence Table with the sequence of each nucleic acid and amino acid sequence.

In Table 1, each section begins with a line that identifies the corresponding internal Ceres clone by its ID number. Subsection (A) then provides information about the nucleotide sequence including the corresponding sequence in Table 2, and the internal Ceres sequence identifier ("Ceres seq_id"). Subsection (B) provides similar information about a polypeptide sequence, but additionally identifies the location of the start codon in the nucleotide sequence which codes for the polypeptide. Subsection (C) provides information (where present) regarding identified domains within the polypeptide and (where present) a name for the polypeptide. Finally, subsection (D) provides (where present) information concerning amino acids which are found to be related and have some sequence identity to the polypeptide sequences of Table 2. Those "related" sequences identified by a "gi" number are in the GenBank® data base (a sequence data base).

TABLE 1

Reference table.
Maximum Length Sequence corresponding to clone ID 23276

(A) Polynucleotide Sequence
    Pat. Appln. SEQ ID NO: 1 (SEQ ID NO: 4307 in U.S. Patent Application No. 60/145,088)
    Ceres seq_id 1389231
(B) Polypeptide Sequence
    Pat. Appln. SEQ ID NO: 2 (SEQ ID NO: 4308 in U.S. Patent Application No. 60/145,088)
    Ceres seq_id 1389232
    Location of start within SEQ ID NO: 1: at 107 nt.
(C) Nomination and Annotation of Domains within Predicted Polypeptide(s)
    Alignment No. 25794
    Mov34 family
    Location within SEQ ID NO: 2: from 25 to 294 aa.
(D) Related Amino Acid Sequences
    Alignment No. 25795
    gi No. 2345100
    % Identity 72.8
    Alignment Length 313
    Location of Alignment in SEQ ID NO: 2: from 1 to 308
    Alignment No. 25796
    gi No. 2345102
    % Identity 80.2
    Alignment Length 121
    Location of Alignment in SEQ ID NO: 2: from 57 to 177
    Alignment No. 25797
    gi No. 2505940
    % Identity 79.9
    Alignment Length 308
    Location of Alignment in SEQ ID NO: 2: from 1 to 308
    Alignment No. 25798
    gi No. 3319432
    % Identity 70.1
    Alignment Length 308
    Location of Alignment in SEQ ID NO: 2: from 1 to 305
    Alignment No. 25799
    gi No. 3334476
    % Identity 70.8
    Alignment Length 309
    Location of Alignment in SEQ ID NO: 2: from 1 to 308
    Alignment No. 25800
    gi No. 497633
    % Identity 70.5
    Alignment Length 309
    Location of Alignment in SEQ ID NO: 2: from 1 to 308
    Alignment No. 25801
    gi No. 5031981
    % Identity 80.3
    Alignment Length 309
    Location of Alignment in SEQ ID NO: 2: from 1 to 308
(B) Polypeptide Sequence
    Pat. Appln. SEQ ID NO: 3 (SEQ ID NO: 4309 in U.S. Patent Application No. 60/145,088)
    Ceres seq_id 1389233
    Location of start within SEQ ID NO: 1: at 224 nt.

TABLE 1-continued

Reference table.
Maximum Length Sequence corresponding to clone ID 23276

(C) Nomination and Annotation of Domains within Predicted Polypeptide(s)
    Alignment No. 25802
    Mov34 family
    Location within SEQ ID NO: 3: from 1 to 255 aa.
(D) Related Amino Acid Sequences
    Alignment No. 25803
    gi No. 2345100
    % Identity 72.8
    Alignment Length 313
    Location of Alignment in SEQ ID NO: 3: from 1 to 269
    Alignment No. 25804
    gi No. 2345102
    % Identity 80.2
    Alignment Length 121
    Location of Alignment in SEQ ID NO: 3: from 18 to 138
    Alignment No. 25805
    gi No. 2505940
    % Identity 79.9
    Alignment Length 308
    Location of Alignment in SEQ ID NO: 3: from 1 to 269
    Alignment No. 25806
    gi No. 3319432
    % Identity 70.1
    Alignment Length 308
    Location of Alignment in SEQ ID NO: 3: from 1 to 266
    Alignment No. 25807
    gi No. 3334476
    % Identity 70.8
    Alignment Length 309
    Location of Alignment in SEQ ID NO: 3: from 1 to 269
    Alignment No. 25808
    gi No. 497633
    % Identity 70.5
    Alignment Length 309
    Location of Alignment in SEQ ID NO: 3: from 1 to 269
    Alignment No. 25809
    gi No. 5031981
    % Identity 80.3
    Alignment Length 309
    Location of Alignment in SEQ ID NO: 3: from 1 to 269
(B) Polypeptide Sequence
    Pat. Appln. SEQ ID NO: 4 (SEQ ID NO: 4310 in U.S. Patent Application No. 60/145,088)
    Ceres seq_id 1389234
    Location of start within SEQ ID NO: 1: at 254 nt.
(C) Nomination and Annotation of Domains within Predicted Polypeptide (s)
    Alignment No. 25810
    Mov34 family
    Location within SEQ ID NO:4: from 1 to 245 aa.
(D) Related Amino Acid Sequences
    Alignment No. 25811
    gi No. 2345100
    % Identity 72.8
    Alignment Length 313
    Location of Alignment in SEQ ID NO: 4: from 1 to 259
    Alignment No. 25812
    gi No. 2345102
    % Identity 80.2
    Alignment Length 121
    Location of Alignment in SEQ ID NO: 4: from 8 to 128
    Alignment No. 25813
    gi No. 2505940
    % Identity 79.9
    Alignment Length 308
    Location of Alignment in SEQ ID NO: 4: from 1 to 259
    Alignment No. 25814
    gi No. 3319432
    % Identity 70.1
    Alignment Length 308
    Location of Alignment in SEQ ID NO: 4: from 1 to 256
    Alignment No. 25815
    gi No. 3334476
    % Identity 70.8
    Alignment Length 309

TABLE 1-continued

Reference table.
Maximum Length Sequence corresponding to clone ID 23276

Location of Alignment in SEQ ID NO: 4: from 1 to 259
Alignment No. 25816
gi No. 497633
% Identity 70.5
Alignment Length 309
Location of Alignment in SEQ ID NO: 4: from 1 to 259

TABLE 1-continued

Reference table.
Maximum Length Sequence corresponding to clone ID 23276

Alignment No. 25817
gi No. 5031981
% Identity 80.3
Alignment Length 309
Location of Alignment in SEQ ID NO: 4: from 1 to 259

TABLE 2

Sequence listing.

(2) INFORMATION FOR SEQ ID NO: 1:

(i) SEQUENCE CHARACTERISTICS:

(A) LENGTH: 1185 base pairs (B) TYPE: nucleic acid (C) STRANDEDNESS: single (D) TOPOLOGY: linear (ii) MOLECULE TYPE: DNA (genomic)

(ix) FEATURE:

(A) NAME/KEY: -

(B) LOCATION: 1 . . . 1185

(D) OTHER INFORMATION: /Ceres Seq. ID 1389231

(xi) SEQUENCE DESCRIPTION: SEQ ID NO: 1:

```
AAACAAAGAA AACTGAGAAA AAGGTTTTCT TATAAGATCC CATTCTTGTA GCAAAAACCC     60
AGAAGAACAA ACTTTCGAAG AAGACGACTA ATCAATTCAT CTGATTATGG AGAGACTACA    120
GAGAATCTTC GGAGCTGGTG GCGGTTTAGG TCACGCATCG CCTGATTCTC CGACTCTCGA    180
TACATCGGAG CAGGTTTACA TCTCTTCTCT CGCTCTCCTC AAGATGCTTA AGCACGGAAG    240
AGCTGGTGTT CCTATGGAAG TCATGGGATT GATGCTTGGA GAGTTTGTGG ATGAGTACAC    300
TGTTAGGGTT GTGGATGTTT TTGCGATGCC TCAGAGTGGT ACTGGTGTTA GTGTTGAAGC    360
TGTTGATCAT GTTTTCCAGA CTAATATGCT CGACATGCTT AAACAGACCG GAAGACCTGA    420
GATGGTGGTT GGTTGGTATC ATTCACATCC TGGATTCGGC TGCTGGCTTT CTGGGGTTGA    480
CATTAATACT CAACAGAGTT TTGAAGCTTT GAATCAGCGA GCTGTAGCAG TGGTGGTAGA    540
TCCGATTCAG AGTGTGAAAG GAAAGGTGGT GATTGATGCG TTCCGCTCCA TAAATCCACA    600
GACCATTATG CTTGGGCACG AACCCCGTCA AACAACATCG AACCTTGGGC ACTTGAACAA    660
ACCATCGATC CAGGCTTTGA TTCACGGGTT GAACAGACAC TATTACTCAA TAGCAATCAA    720
CTATAGGAAG AACGAGCTTG AGGAGAAGAT GTTACTCAAC CTCCACAAGA GAAATGGAC    780
AGATGGTCTG ACGCTAAGAC GCTTTGACAC CCACTCCAAG ACCAACGAAC AGACGGTCCA    840
GGAGATGTTG AGCTTGGCTG CTAAATATAA CAAGGCGGTT CAAGAGGAGG ACGAGTTGTC    900
ACCAGAGAAG CTGGCAATTG TGAATGTGGG AAGACAAGAT GCAAAGAAGC ATCTGGAAGA    960
ACATGTCTCG AACCTCATGT CATCCAACAT TGTTCAGACA CTAGGCACTA TGCTCGACAC   1020
TGTTGTCTTC TAGAGAGCTT ACTTCTCCAG CCGCTTCAAG TCATTGAGCT TTGTTCTTCT   1080
GCATCTCTTT GGCTTCTACT GAATGTTCTC TTTTTATCTG CTAGCTTTTT ACAAGGTTGT   1140
```

TABLE 2-continued

Sequence listing.

ACTGTACTAT GTGATTTCGT TCGTTAAGGG CAGGGATCGA TTTCC (2) INFORMATION FOR SEQ ID NO: 2:

(i) SEQUENCE CHARACTERISTICS:

(A) LENGTH: 308 amino acids (B) TYPE: amino acid (C) STRANDEDNESS:

(D) TOPOLOGY: linear (ii) MOLECULE TYPE: peptide (ix) FEATURE:

(A) NAME/KEY: peptide (B) LOCATION: 1 . . . 308

(D) OTHER INFORMATION: /Ceres Seq. ID 1389232

(xi) SEQUENCE DESCRIPTION: SEQ ID NO: 2:

```
Met Glu Arg Leu Gln Arg Ile Phe Gly Ala Gly Gly Leu Gly His
1               5                   10                  15

Ala Ser Pro Asp Ser Pro Thr Leu Asp Thr Ser Glu Gln Val Tyr Ile
            20                  25                  30

Ser Ser Leu Ala Leu Leu Lys Met Leu Lys His Gly Arg Ala Gly Val
            35                  40                  45

Pro Met Glu Val Met Gly Leu Met Gly Glu Phe Val Asp Glu Tyr
    50                  55                  60

Thr Val Arg Val Val Asp Val Phe Ala Met Pro Gln Ser Gly Thr Gly
65                  70                  75                  80

Val Ser Val Glu Ala Val Asp His Val Phe Gln Thr Asn Met Leu Asp
            85                  90                  95

Met Leu Lys Gln Thr Gly Arg Pro Glu Met Val Val Gly Trp Tyr His
            100                 105                 110

Ser His Pro Gly Phe Gly Cys Trp Leu Ser Gly Val Asp Ile Asn Thr
    115                 120                 125

Gln Gln Ser Phe Glu Ala Leu Asn Gln Arg Ala Val Ala Val Val Val
    130                 135                 140

Asp Pro Ile Gln Ser Val Lys Gly Lys Val Val Ile Asp Ala Phe Arg
145                 150                 155                 160

Ser Ile Asn Pro Gln Thr Ile Met Leu Gly His Glu Pro Arg Gln Thr
                165                 170                 175

Thr Ser Asn Leu Gly His Leu Asn Lys Pro Ser Ile Gln Ala Leu Ile
            180                 185                 190

His Gly Leu Asn Arg His Tyr Tyr Ser Ile Ala Ile Asn Tyr Arg Lys
        195                 200                 205

Asn Glu Leu Glu Glu Lys Met Leu Leu Asn Leu His Lys Lys Lys Trp
210                 215                 220

Thr Asp Gly Leu Thr Leu Arg Arg Phe Asp Thr His Ser Lys Thr Asn
225                 230                 235                 240

Glu Gln Thr Val Gln Glu Met Leu Ser Leu Ala Ala Lys Tyr Asn Lys
                245                 250                 255

Ala Val Gln Glu Glu Asp Glu Leu Ser Pro Glu Lys Leu Ala Ile Val
            260                 265                 270
```

TABLE 2-continued

Sequence listing.

Asn Val Gly Arg Gln Asp Ala Lys Lys His Leu Glu Glu His Val Ser
        275                 280                 285

Asn Leu Met Ser Ser Asn Ile Val Gln Thr Leu Gly Thr Met Leu Asp
        290                 295                 300

Thr Val Val Phe
305

(2) INFORMATION FOR SEQ ID NO: 3:

(i) SEQUENCE CHARACTERISTICS:

(A) LENGTH: 269 amino acids (B) TYPE: amino acid (C) STRANDEDNESS:

(D) TOPOLOGY: linear (ii) MOLECULE TYPE: peptide (ix) FEATURE:

(A) NAME/KEY: peptide (B) LOCATION: 1 . . . 269

(D) OTHER INFORMATION: /Ceres Seq. ID 1389233

(xi) SEQUENCE DESCRIPTION: SEQ ID NO: 3:

Met Leu Lys His Gly Arg Ala Gly Val Pro Met Glu Val Met Gly Leu
1               5                   10                  15

Met Leu Gly Glu Phe Val Asp Glu Tyr Thr Val Arg Val Val Asp Val
        20                  25                  30

Phe Ala Met Pro Gln Ser Gly Thr Gly Val Ser Val Glu Ala Val Asp
        35                  40                  45

His Val Phe Gln Thr Asn Met Leu Asp Met Leu Lys Gln Thr Gly Arg
        50                  55                  60

Pro Glu Met Val Val Gly Trp Tyr His Ser His Pro Gly Phe Gly Cys
65                  70                  75                  80

Trp Leu Ser Gly Val Asp Ile Asn Thr Gln Gln Ser Phe Glu Ala Leu
                85                  90                  95

Asn Gln Arg Ala Val Ala Val Val Val Asp Pro Ile Gln Ser Val Lys
                100                 105                 110

Gly Lys Val Val Ile Asp Ala Phe Arg Ser Ile Asn Pro Gln Thr Ile
        115                 120                 125

Met Leu Gly His Glu Pro Arg Gln Thr Thr Ser Asn Leu Gly His Leu
        130                 135                 140

Asn Lys Pro Ser Ile Gln Ala Leu Ile His Gly Leu Asn Arg His Tyr
145                 150                 155                 160

Tyr Ser Ile Ala Ile Asn Tyr Arg Lys Asn Glu Leu Glu Glu Lys Met
                165                 170                 175

Leu Leu Asn Leu His Lys Lys Lys Trp Thr Asp Gly Leu Thr Leu Arg
                180                 185                 190

Arg Phe Asp Thr His Ser Lys Thr Asn Glu Gln Thr Val Gln Glu Met
        195                 200                 205

Leu Ser Leu Ala Ala Lys Tyr Asn Lys Ala Val Gln Glu Glu Asp Glu
        210                 215                 220

Leu Ser Pro Glu Lys Leu Ala Ile Val Asn Val Gly Arg Gln Asp Ala
225                 230                 235                 240

TABLE 2-continued

Sequence listing.

```
Lys Lys His Leu Glu Glu His Val Ser Asn Leu Met Ser Ser Asn Ile
            245                 250                 255

Val Gln Thr Leu Gly Thr Met Leu Asp Thr Val Val Phe
            260                 265
```

(2) INFORMATION FOR SEQ ID NO: 4:

(i) SEQUENCE CHARACTERISTICS:

(A) LENGTH: 259 amino acids (B) TYPE: amino acid (C) STRANDEDNESS:

(D) TOPOLOGY: linear (ii) MOLECULE TYPE: peptide (ix) FEATURE:

(A) NAME/KEY: peptide (B) LOCATION: 1 . . . 259

(D) OTHER INFORMATION: /Ceres Seq. ID 1389234

(xi) SEQUENCE DESCRIPTION: SEQ ID NO: 4:

```
Met Glu Val Met Gly Leu Met Leu Gly Glu Phe Val Asp Glu Tyr Thr
1               5                   10                  15

Val Arg Val Val Asp Val Phe Ala Met Pro Gln Ser Gly Thr Gly Val
            20                  25                  30

Ser Val Glu Ala Val Asp His Val Phe Gln Thr Asn Met Leu Asp Met
            35                  40                  45

Leu Lys Gln Thr Gly Arg Pro Glu Met Val Val Gly Trp Tyr His Ser
        50                  55                  60

His Pro Gly Phe Gly Cys Trp Leu Ser Gly Val Asp Ile Asn Thr Gln
65                  70                  75                  80

Gln Ser Phe Glu Ala Leu Asn Gln Arg Ala Val Ala Val Val Val Asp
            85                  90                  95

Pro Ile Gln Ser Val Lys Gly Lys Val Val Ile Asp Ala Phe Arg Ser
            100                 105                 110

Ile Asn Pro Gln Thr Ile Met Leu Gly His Glu Pro Arg Gln Thr Thr
            115                 120                 125

Ser Asn Leu Gly His Leu Asn Lys Pro Ser Ile Gln Ala Leu Ile His
            130                 135                 140

Gly Leu Asn Arg His Tyr Tyr Ser Ile Ala Ile Asn Tyr Arg Lys Asn
145                 150                 155                 160

Glu Leu Glu Glu Lys Met Leu Leu Asn Leu His Lys Lys Lys Trp Thr
            165                 170                 175

Asp Gly Leu Thr Leu Arg Arg Phe Asp Thr His Ser Lys Thr Asn Glu
            180                 185                 190

Gln Thr Val Gln Glu Met Leu Ser Leu Ala Ala Lys Tyr Asn Lys Ala
            195                 200                 205

Val Gln Glu Glu Asp Glu Leu Ser Pro Glu Lys Leu Ala Ile Val Asn
            210                 215                 220

Val Gly Arg Gln Asp Ala Lys Lys His Leu Glu Glu His Val Ser Asn
225                 230                 235                 240
```

TABLE 2-continued

Sequence listing.

Leu Met Ser Ser Asn Ile Val Gln Thr Leu Gly Thr Met Leu Asp Thr
                245                 250                 255

Val Val Phe

DETAILED DESCRIPTION OF THE INVENTION

The invention relates to (I) polynucleotides and methods of use thereof, such as IA. Probes & Primers;
IB. Methods of Detection & Isolation;
  B.1. Hybridization;
  B.2. Methods of Mapping;
  B.3. Southern Blotting;
  B.4. Isolating cDNA from Related Organisms;
  B.5. Isolating and/or Identifying Orthologous Genes
IC. Methods of Inhibiting Gene Expression
  C.1. Antisense
  C.2. Ribozyme Constructs;
  C.3. Co-Suppression;
  C.4. Other Methods to Inhibit Gene Expression
ID. Methods of Functional Analysis;
IE. Promoter Sequences and Their Use;
IF. UTR's and/or Intron Sequences and Their Use; and
IG. Coding Sequences and Their Use.

The specification also discloses (II) polypeptides including, without limitation, native proteins, mutants, fragments, and fusions. Antibodies to said polypeptides are also disclosed.

The specification further discloses (III) methods of modulating polypeptide production or activity. Examples of such methods include (i) suppressed, (ii) enhanced, and (iii) directed expression.

The application further describes (IV) gene constructs, expression vectors, and (V) transformation procedures to illustrate the invention by way of examples.

I. Polynucleotides

A number of the nucleotide sequences disclosed in Table 2 of the priority patent applications as representative of the SDFs of the invention can be obtained by sequencing genomic DNA (gDNA) and/or cDNA from corn plants grown from HYBRID SEED # 35A19, purchased from Pioneer Hi-Bred International, Inc., Supply Management, P.O. Box 256, Johnston, Iowa 50131-0256.

SDFs of the invention represent portions of the genome of corn or *Arabidopsis* and/or represent mRNA expressed from that genome. The isolated nucleic acid of the invention also encompasses corresponding portions of the genome and/or cDNA complement of other organisms as described in detail below.

Starting material for cDNA synthesis for the exemplary corn cDNA clones having sequences presented in Table 2 of a priority patent application was poly(A)-containing polysomal mRNAs from the inflorecence tissues of corn plants grown from HYBRID SEED # 35A19. Male inflorescences and female inflorescences isolated at various stages of development (pre-and post fertilization), and root tissue was used. Selection for poly(A) containing polysomal RNA was done using oligo d(T) cellulose columns, as described by Cox and Goldberg, "Plant Molecular Biology: A Practical Approach", pp. 1-35, Shaw ed., c. 1988 by IRL, Oxford.

Each tissue individually was pulverized and exposed to liquid nitrogen. Next, the samples were homogenized in the presence of detergents and then centrifuged. The debris and nuclei were removed from the sample, and more detergents were added to the sample. The sample was centrifuged, and the debris was removed. Then the sample was applied to a 2M sucrose cushion to isolate polysomes. The RNA was isolated by treatment with detergents and proteinase K followed by ethanol precipitation and centrifugation.

The polysomal RNA from the different tissues was pooled according to the following mass ratios: 15/15/1 for respectively male inflorescence, female inflorescence and root. The pooled material was then used for cDNA synthesis by the methods described below.

The quality and the integrity of the polyA$^+$ RNAs were checked. Northern blots hybridized with a globin probe were used to confirm that the mRNAs were not degraded. Contamination of the polyA$^+$ mRNAs by ribosomal sequences was checked using Northern blots and a probe derived from the sequence of the 28S rRNA. Preparations of mRNAs with less than 5% of rRNAs were used in library construction. To avoid constructing libraries with RNAs contaminated by exogenous sequences (prokaryotic or fungal), the presence of bacterial 16S ribosomal sequences or of two highly expressed fungal mRNAs was examined using PCR.

A number of the nucleotide sequences disclosed in Table 2 of the priority patent applications as representative of the SDFs of the invention can also be obtained by sequencing genomic DNA from *Arabidopsis thaliana*, Wassilewskija ecotype or by sequencing cDNA obtained from mRNA from such plants as described below. This is a true breeding strain. Seeds of the plant are available from the *Arabidopsis* Biological Resource Center at the Ohio State University, under the accession number CS2360.

Starting material for cDNA synthesis for the exemplary *Arabidopsis* cDNA clones having sequences presented in Table 2 of a priority patent application was polysomal RNA was isolated from the inflorescence tissues (the very top apex of the plant) of *Arabidopsis thaliana* Landsberg erecta (L. er.) also obtained from the *Arabidopsis* Biological Resource Center. Nine parts of the inflorescence to every part of root was used, as measured by mass. Tissue was pulverized and exposed to liquid nitrogen. Next, the sample was homogenized in the presence of detergents and then centrifuged. The debris and nuclei were removed from the sample, and more detergents were added to the sample. The sample was centrifuged, and the debris was removed, and the sample was applied to a 2M sucrose cushion to isolate polysomal RNA. Cox et al., "Plant Molecular Biology: A Practical Approach", pp. 1-35, Shaw ed., c. 1988 by IRL, Oxford. The polysomal RNA was used for cDNA synthesis by the methods described below. Polysomal mRNA was then isolated as described above for isolation of corn cDNA. The quality of the RNA was assessed electrophoretically.

Following preparation of the mRNAs from various tissues as described above, selection of mRNA with intact 5' ends and specific attachment of an oligonucleotide tag to the 5' end of such mRNA is performed using either a chemical or enzymatic approach. Both techniques take advantage of the presence of the "cap" structure, which characterizes the 5'end of intact mRNAs and which comprises a guanosine generally methylated once, at the 7 position.

The chemical modification approach involves the optional elimination of the 2',3'-cis diol of the 3' terminal ribose, the oxidation of the 2',3',-cis diol of the ribose linked to the cap of the 5' ends of the mRNAs into a dialdehyde, and the coupling of the such obtained dialdehyde to a derivatized oligonucleotide tag. Further details regarding the chemical approaches for obtaining mRNAs having intact 5' ends are disclosed in International Application No. WO96/34981 published Nov. 7, 1996.

The enzymatic approach for ligating the oligonucleotide tag to the 5' ends of mRNAs with intact 5' ends involves the removal of the phosphate groups present on the 5' ends of uncapped incomplete mRNAs, the subsequent decapping of mRNAs with intact 5' ends and the ligation of the phosphate present at the 5' end of the decapped mRNA to an oligonucleotide tag. Further details regarding the enzymatic approaches for obtaining mRNAs having intact 5' ends are disclosed in Dumas Milne Edwards J. B. (Doctoral Thesis of Paris VI University, Le clonage des ADNc complets: difficultes et perspectives nouvelles. Apports pour l'etude de la regulation de l'expression de la tryptophane hydroxylase de rat, 20 Dec. 1993), EPO 625572, and Kato et al., Gene 150:243-250 (1994).

In either the chemical or the enzymatic approach, the oligonucleotide tag has a restriction enzyme site (e.g., an EcoRI site) therein to facilitate later cloning procedures. Following attachment of the oligonucleotide tag to the mRNA, the integrity of the mRNA is then examined by performing a Northern blot using a probe complementary to the oligonucleotide tag.

For the mRNAs joined to oligonucleotide tags using either the chemical or the enzymatic method, first strand cDNA synthesis is performed using reverse transcriptase with an oligo-dT primer. This oligo-dT primer can contain an internal tag of at least 4 nucleotides, which can be from one mRNA preparation to another. In order to protect internal EcoRI sites in the cDNA from digestion at later steps in the procedure, methylated dCTP is used for first strand synthesis. After removal of RNA by an alkaline hydrolysis, the first strand of cDNA is precipitated using isopropanol in order to eliminate residual primers.

The second strand of the cDNA is then synthesized with a DNA polymerase, such as Klenow fragment, using a primer corresponding to the 5' end of the ligated oligonucleotide. Preferably, the primer is typically 20-25 bases in length. Methylated dCTP is used for second strand synthesis in order to protect internal EcoRI sites in the cDNA from digestion during the cloning process.

Following second strand synthesis, the full-length cDNAs are cloned into a phagemid vector, such as pBlueScript™ (Stratagene). The ends of the full-length cDNAs are blunted with T4 DNA polymerase (Biolabs) and the cDNA is digested with EcoRI. Since methylated dCTP is used during cDNA synthesis, the EcoRI site present in the tag is the only hemimethylated site; hence the only site susceptible to EcoRI digestion. In some instances, to facilitate subcloning, an Hind III adaptor is added to the 3' end of full-length cDNAs.

The full-length cDNAs are then size fractionated using either exclusion chromatography (AcA, Biosepra) or electrophoretic separation which yields 3 to 6 different fractions. The full-length cDNAs are then directionally cloned either into pBlueScript™ using either the EcoRI and SmaI restriction sites or the EcoRI and Hind III restriction sites when the Hind III adaptator is present in the full-length cDNAs. The ligation mixture is transformed into bacteria, preferably by electrophoration, and propagated under appropriate antibiotic selection.

Clones containing the oligonucleotide tag attached to full-length cDNAs are then selected as follows. The plasmid DNAs containing cDNA libraries made as described above are purified (e.g., by a column available from Qiagen). A positive selection of the tagged clones is performed as follows. Briefly, in this selection procedure, the plasmid DNA is converted to single stranded DNA using gene II endonuclease of the phage F1 in combination with an exonuclease (Chang et al., Gene 127:95 (1993)) such as exonuclease III or T7 gene 6 exonuclease. The resulting single stranded DNA is then purified using paramagnetic beads as described by Fry et al., Biotechniques, 13: 124 (1992.) In this procedure, the single stranded DNA is hybridized with a biotinylated oligonucleotide having a sequence corresponding to the 3' end of the oligonucleotide tag described in Example 2. Preferably, the primer has a length of 20-25 bases. Clones including a sequence complementary to the biotinylated oligonucleotide are selected by incubation with streptavidin coated magnetic beads followed by magnetic capture. After capture of the positive clones, the plasmid DNA is released from the magnetic beads and converted into double stranded DNA using a DNA polymerase such as the ThermoSequenase obtained from Amersham Pharmacia Biotech. Alternatively, protocols such as the Gene Trapper kit (Gibco BRL) may be used. The double stranded DNA is then transformed, preferably by electroporation into bacteria. The percentage of positive clones having the 5' tag oligonucleotide is estimated to be typically between 90 and 98% using dot blot analysis.

Following transformation, the libraries are ordered in microtiter plates and sequenced.

Other methods for cloning full-length cDNA are described, for example, by Seki et al., Plant Journal 15(5): 707-720 (1998) entitled "High-efficiency cloning of *Arabidopsis* full-length cDNA by biotinylated Cap trapper"; Maruyama et al., Gene 138:171 (1994) entitled "Oligo-capping a simple method to replace the cap structure of eukaryotic mRNAs with oligoribonucleotides"; and WO 96/34981.

It is contemplated that the nucleotide sequences presented herein may contain some small percentage of errors. These errors may arise in the normal course of determination of nucleotide sequences. Sequence errors can be corrected by obtaining seeds deposited under the accession numbers cited above, propagating them, isolating genomic DNA or appropriate mRNA from the resulting plants or seeds thereof, amplifying the relevant portion of the genomic DNA or mRNA using primers having a sequence that flanks the erroneous sequence, and sequencing the amplification product.

I.A. Probe & Primers

Probes and primers of the instant invention will hybridize to a polynucleotide comprising a sequence in Table 2. Though many different nucleotide sequences can encode an amino acid sequence, in some instances, the sequences of Table 2 are preferred for encoding polypeptides of the invention. However, the sequence of the probes and/or primers of the instant invention need not be identical to those in Table 2 or the complements thereof. Some variation in the sequence and length can lead to increase assay sensitivity if the nucleic acid probe can form a duplex with a target nucleotide in a sample that can be detected or isolated. The probes and/or primers of the invention can include additional nucleotides that may be helpful as a label to detect the formed duplex or for later cloning purposes.

Probe length will vary depending on the application. For use as a PCR primer, probes should be 12-40 nucleotides, preferably 18-30 nucleotides long. For use in mapping, probes should be 50 to 500 nucleotides, preferably 100-250 nucleotides long. For Southern hybridizations, probes as long as several kilobases can be used as explained below.

The probes and/or primers can be produced by synthetic procedures such as the triester method of Matteucci et al. *J. Am. Chem. Soc.* (1981) 103: 3185; or according to Urdea et al., *Proc. Natl. Acad.* 80: 7461 (1981) or using commercially available automated oligonucleotide synthesizers.

I.B. Methods of Detection & Isolation

B.1. Hybridization

Probes and/or primers can be used either for detection and/or isolation of polynucleotide sequences. Such polynucleotides are included in the subject matter of the invention. Depending on the stringency of the conditions under which these probes and/or primers are used, polynucleotides exhibiting a wide range of similarity to those in Table 2 can be detected or isolated.

"Stringency" is a function of probe length, probe composition (G+C content), and hybridization or wash conditions of salt concentration, organic solvent concentration, and temperature. Stringency is typically compared by the parameter "Tm", which is the temperature at which 50% of the complementary molecules in the hybridization are hybridized, in terms of a temperature differential from Tm. High stringency conditions are those providing a condition of Tm−5° C. to Tm−10° C. Medium stringency conditions are those providing Tm−20° C. to Tm−29° C. Low stringency conditions are those providing a condition of Tm−40° C. to Tm−48° C. The relationship of hybridization conditions to Tm (in ° C.) is expressed in the mathematical equation $$Tm = 81.5 - 16.6(\log 10[Na+]) + 0.41(\%G+C) - (600/N) \quad (1)$$

where N is the length of the probe. This equation works well for probes 14 to 70 nucleotides in length that are identical to the target sequence. For probes of 50 nucleotides to greater than 500 nucleotides, and conditions that include an organic solvent (formamide) an alternative formulation for Tm of DNA-DNA hybrids is useful.

$$Tm = 81.5 + 16.6 \log \{[Na+]/(1+0.7[Na+])\} + 0.41(\%G+C) - 500/L 0.63(\% \text{ formamide}) \quad (2)$$

where L is the length of the probe in the hybrid (P. Tijessen, "Hybridization with Nucleic Acid Probes" in Laboratory Techniques in Biochemistry and Molecular Biology, P. C. vand der Vliet, ed., c. 1993 by Elsevier, Amsterdam). With respect to equation (2), Tm is affected by the nature of the hybrid; for DNA-RNA hybrids Tm is 10-15° C. higher than calculated, for RNA-RNA hybrids Tm is 20-25° C. higher. Most importantly for use of hybridization to identify DNA including genes corresponding to SDFs, Tm decreases about 1° C. for each 1% decrease in homology when a long probe is used (Bonner et al., *J. Mol. Biol.* 81:123 (1973)).

Equation (2) is derived under assumptions of equilibrium and therefore, hybridizations according to the present invention are most preferably performed under conditions of probe excess and for sufficient time to achieve equilibrium. The time required to reach equilibrium can be shortened by inclusion of a "hybridization accelerator" such as dextran sulfate or another high volume polymer in the hybridization buffer.

When the practitioner wishes to examine the result of membrane hybridizations under a variety of stringencies, an efficient way to do so is to perform the hybridization under a low stringency condition, then to wash the hybridization membrane under increasingly stringent conditions. With respect to wash steps preferred stringencies lie within the ranges stated above; high stringency is 5-8° C. below Tm, medium stringency is 26-29° C. below Tm and low stringency is 45-48° C. below Tm.

A number of methods known to those skilled in the art can be used with the probes and/or primers of the invention to isolate and detected polynucleotides, including, without limitation: Southerns, Northerns, Branched DNA hybridization assays, polymerase chain reaction, and variations thereof.

When using SDFs to identify orthologous genes in other species, the practitioner will preferably adjust the amount of target DNA of each species so that, as nearly as is practical, the same number of genome equivalents are present for each species examined. This prevents faint signals from species having large genomes, and thus small numbers of genome equivalents per mass of DNA, from erroneously being interpreted as lack of the presence of the corresponding gene in the genome.

A good general discussion of the factors for determining hybridization conditions is provided by Sambrook et al. (Molecular Cloning, a Laboratory Manual, 2nd ed., c. 1989 by Cold Spring Harbor Laboratory Press, Cold Spring Harbor, N.Y.; see esp., chapters 11 and 12). Additional considerations and details of the physical chemistry of hybridization are provided by G. H. Keller and M. M. Manak "DNA Probes", 2nd Ed. pp. 1-25, c. 1993 by Stockton Press, New York, N.Y.

Hybridization of one nucleic acid to another constitutes a physical property that defines the subject SDF of the invention. Also, such hybridization imposes structural limitations on the pair. For example, for a probe molecule, given that the sequence of the probe nucleic acid is known and fixed, equation (2) indicates that the combined variation in GC content of the target DNA and mismatch between the probe and the hybridizing DNA is determined for any given hybridization buffer composition and Tm.

The probes and/or primers of the instant invention can be used to detect or isolate nucleotides that are "identical" to the probes or primers. Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence can form a Watson-Crick base pair with a reference polynucleotide sequence. Complementary sequences can include nucleotides, such as inosine, that do not disrupt Watson-Crick base pairing, but also do not contribute to the pairing.

Optimal alignment of sequences for comparison may be conducted by the local homology algorithm of Smith and Waterman Add. APL. Math. 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

The probes and/or primers or the invention can also be used to detect and/or isolate polynucleotides exhibiting at least 80% sequence identity with the sequences of Table 2 or fragments thereof. "Percentage of sequence identity" is determined by comparing two optimally aligned sequences over a comparison window, wherein the portion of the polynucleotide sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Isolated polynucleotides within the scope of the invention also include allelic variants of the specific sequences presented in Table 2. An "allelic variant" is a sequence that is a variant from that of the SDF, but represents the same chromosomal locus in the organism. In addition to those that occur by normal genetic variation in a population and are perhaps fixed in the population by standard breeding methods, allelic variants can be produced by genetic engineering methods. A preferred allelic variant is one that is found in a naturally occurring plant, including a laboratory cultivar or ecotype. Allelic variants are either silent or expressed. A silent allele is one that does not affect the phenotype of the organism. An expressed allele results in a detectable change in the phenotype of the trait represented by the locus. Alleles can occur in any portion of the genome, including regulatory regions as well as structural genes.

As is apparent from the above explanation, the SDFs of the invention encompass minor variation in the nucleotide and amino acid sequences presented in Table 2. With respect to nucleotide sequences, degeneracy of the genetic code provides the possibility to substitute at least one base of the base sequence of a gene by a different base without causing the amino acid sequence of the polypeptide produced from the gene to be changed. Hence, the DNA of the present invention may also have any base sequence that has been changed from a sequence in Table 2 by substitution in accordance with degeneracy of the genetic code. References describing codon usage include: Carels et al., *J. Mol. Evol.* 46: 45 (1998) and Fennoy et al., *Nucl. Acids Res.* 21(23): 5294 (1993).

B.2. Mapping

The isolated DNA of the invention can be used to physically map particular clones representing corn or *Arabidopsis* DNA to their representative genomes. In this embodiment of the invention, the cloned DNA of interest is hybridized to a panel of SDFs of the invention.

First, SDFs of the invention are assigned to Bacterial Artificial Chromosome (BAC) or Yeast Artificial Chromosome (YAC) clones, preferably clones that have been ordered as a contig library. Then, the SDFs are arrayed on a filter, preferably in a logical order that reflects their physical arrangement in the genome. That is, SDFs that are proximate to each other in the genome are also located next to each other on the filter and the ordering of the SDFs in the genome is similarly reflected on the filter. Hybridization of the particular DNA to particular SDFs thus identifies those BAC(s) which contain DNA having a nucleotide sequence similar or identical to that of the particular DNA of interest. Thus, the DNA of interest is quickly located on the physical map of the corn or *Arabidopsis* genome.

If the DNA of interest is known to provide, or at least to influence, a particular phenotypic trait, then the phenotypic trait is also thus quickly ordered on the physical map and linkage is established to other mapped traits.

The cloned DNA of the invention can also be used to establish markers for genetic traits. The SDFs can be used as probes to identify polymorphisms in the genome of ecotypes, preferably recombinant inbred ecotypes, having different alleles of at least two particular traits. Then, genotyping of these parental ecotypes can be performed and the genotypes compared to F1 recombinants between the traits. The frequency of recombination between the polymorphisms and between the phenotypic traits is analyzed to identify those polymorphisms that are most often, preferably always, transmitted together with the phenotypic trait.

Use of recombinant inbred lines for genetic mapping in *Arabidopsis* is described by Alonso-Blanco et al., Methods in Molecular Biology, vol. 82, "*Arabidopsis* Protocols", pp. 137-146, J. M. Martinez-Zapater and J. Salinas, eds., c. 1998 by Humana Press, Totowa, N.J.

Use of recombinant inbred lines for genetic mapping in corn is described by Burr ("Mapping Genes with Recombinant Inbreds, pp. 249-254 in Freeling, M. and V. Walbot (Ed.). The Maize Handbook, c. 1994 by Springer-Verlag New York, Inc.: New York, N.Y., USA; Berlin, Germany; Burr et al., *Genetics*, 118:519 (1998); and Gardiner, J. et al., *Genetics*, 134:917 (1993)).

The use of the SDFs of the present invention for simple sequence repeat mapping in the corn genome or in the genome of a related crop such as e.g. rice, is described in Morgante et al. *The Plant J.*, 3:175 (1993); Panaud et al., *Genome*, 38:1170 (1995); Senior et al., *Crop Sci.*, 36:1676 (1996); Taramino et al., *Genome*, 39:277 (1996); and Ahn et al., *Molecular and General Genetics*, 241:483-90 (1993).

In the most preferred instance, the relevant polymorphism will be found within the sequence of an SDF, and this sequence will be the basis for designing differential probes for different alleles. For example, sequence mismatches can be exploited to provide diagnostics based on polymerase chain reaction or ligation-amplification approaches (K. J. Williams et al., *Genome*, 39: 798 (1996), and R. A. Guilfoyle, *Nucleic Acids Res.*, 25:1854 (1997)). Tandem repeats of simple sequences or variable number tandem repeats and the like can be identified by hybridization or polymerase chain reaction assays. (U.S. Pat. No. 5,766,847; and U. H. Refseth et al., *Electrophoresis*, 18: 1519 (1997)). Hybridization to arrays of oligonucleotides can be used to scan multiple alleles of a plurality of loci. (U.S. Pat. Nos. 5,445,934 and 5,410,270 and WO95/35505).

B.3 Southern Blot Hybridization

Hybridization techniques using sequences from Table 2 as probes or primers are a means of detecting target polynucleotides in a sample. These assays can be used to determine if transgenic plants, seeds, or host cells harbor the gene or sequence of interest and therefore will exhibit the trait, phenotype, etc. of interest.

In addition, the hybridization of the SDFs of the invention to nucleic acids obtained from other organisms can be used to identify orthologous genes from other species and/or additional members of gene families either in the same or different species. In regard to identifying genes in other species, a Southern blot of genomic DNA provides description of isolated DNA fragments that comprise the orthologous genes or additional members of the gene families. That is, given such data, one of ordinary skill in the art could distinguish the isolated DNA fragments by their size together with the restriction sites at each end and by the property of hybridizing with the SDF probe under the stated conditions.

Southern blots can also be used to generate a map of the portion of the genome of the other species that includes the DNA corresponding to the SDF. Such a map provides additional information about the relative positions of restriction sites within fragments, further distinguishing mapped DNA from the remainder of the genome.

At least two single digestions of the genomic DNA by restriction enzymes, and a double digestion with both, are preferable to make a simple map. Preferably additional enzymes and their combinations will be used to generate a map having more detail. In the event that ambiguities are found in the simple map, they can usually be resolved by repeating the experiment using additional enzymes. Digestions with a single enzyme, especially together with hybridization to a probe sequence, can be used to at least distinguish individual restriction fragments from the remainder of the genome.

Probes for Southern blotting can range in size from 15 to 20 nucleotides to several thousand nucleotides. More preferably, the probe is 100 to 1000 nucleotides long for identifying members of a gene family when it is found that repetitive sequences would complicate the hybridization. For identifying an entire corresponding gene in another species, the probe is more preferably the length of the gene, typically 2000 to 10,000 nucleotides, but probes 50-1,000 nucleotides long might be used. Some genes, however, might require probes up to 15,000 nucleotides long or overlapping probes constituting the full-length sequence to span their lengths.

Also, while it is preferred that the probe be homogeneous with respect to its sequence, that is not necessary. For example, as described below, a probe representing members of a gene family having diverse sequences can be generated using PCR to amplify genomic DNA or RNA templates using primers derived from SDFs that include sequences that define the gene family.

For identifying corresponding genes in another species, the probe for Southern blotting most preferably would be the genomic copy of the probe gene. This allows all elements of the gene to be identified in the other species. The next most preferable probe is a cDNA spanning the entire coding sequence, which allows all of the mRNA-coding portion of the gene to be identified; in this case it can occur that some introns in the gene might be missed. Probes for Southern blotting can be easily generated from SDFs by making primers having the sequence at the ends of the SDF and using corn or *Arabidopsis* genomic DNA as a template. In instances where the SDF includes sequence conserved among species, primers including the conserved sequence can be applied to PCR using genomic DNA from a species of interest to obtain a probe. Similarly, if the SDF includes a domain of interest, that portion of the SDF can be used to make primers and the appropriate template DNA used to make a probe for genes including the domain. Alternatively, the PCR products can be resolved, for example by gel electrophoresis, and cloned and/or sequenced. In this manner, the variants of the domain among members of a gene family, both within and across species, can be examined.

B.4.1 Isolating DNA from Related Organisms

The SDFs of the invention can be used to isolate the corresponding DNA from other organisms. Either cDNA or genomic DNA can be isolated. For isolating genomic DNA, a lambda, cosmid, BAC or YAC genomic library from the plant of interest can be constructed using standard molecular biology techniques as described in detail by Sambrook et al. 1989 (Molecular cloning: A laboratory manual, 2nd ed. Cold Spring Harbor Laboratory Press, New York) and by Ausubel et al. 1992 (Current Protocols in Molecular Biology, Greene Publishing, New York).

To screen a phage library recombinant lambda clones are plated out on appropriate bacterial medium using an appropriate *E. coli* host strain. The resulting plaques are lifted from the plates using nylon or nitrocellulose filters. The plaque lifts are processed through denaturation, neutralization, and washing treatments following the standard protocols outlined by Ausubel et al. (1992). The plaque lifts are hybridized to either radioactively labeled or non-radioactively labeled SDF DNA at room temperature for about 16 hours usually in the presence of 50% formamide and 5×SSC (sodium chloride and sodium citrate) buffer and blocking reagents. The plaque lifts are then washed at 42° C. with 1% Sodium Dodecyl Sulfate (SDS) and at a particular concentration of SSC. The SSC concentration to be used is dependent upon the stringency at which the hybridization was observed in initial Southern blot analysis performed. For example, if a hybridizing fragment can be observed under medium stringency (e.g., Tm−20° C.), then this condition is maintained or preferably adjusted to a less stringent condition (e.g., Tm-30° C.) to wash the plaque lifts. The plaque lifts are exposed to X-ray films to detect the positive clones, which are then subsequently isolated for purification using the same general protocol outlined above. Once the clone is purified, restriction analysis can be done to narrow the region corresponding to the gene of interest. The restriction analysis and succeeding subcloning steps can be done using procedures described by, for example Sambrook et al. (1989) cited above.

To screen a YAC library, the procedures outlined for the lambda library are essentially similar except the YAC clones are harbored in bacterial colonies. The YAC clones are plated out at reasonable density on nitrocellulose or nylon filters supported by appropriate bacterial medium in petri plates. Following the growth of the bacterial clones, the filters are then processed through the denaturation, neutralization, and washing steps following the procedures of Ausubel et al. 1992. The same hybridization procedures for lambda library screening are followed.

To isolate cDNA, similar procedures using appropriately modified vectors are employed. For instance, the library can be constructed in a lambda vector appropriate for cloning cDNA such as λgt11. Alternatively, the cDNA library can be made in a plasmid vector. cDNA for cloning can be prepared by any of the methods known in the art, but is preferably prepared as described above. Preferably a cDNA library will include a high proportion of full-length clones.

B.5. Isolating and/or Identifying Orthologous Genes

Probes and primers of the invention can be used to identify and/or isolate polynucleotides related to those in Table 2. Related polynucleotides are those that are native to other plant organisms and exhibit either similar sequence or encode polypeptides with similar biological activity. One specific example is an orthologous gene, a gene that has a high degree of sequence similarity, often along the entire length of the coding portion of the gene, and also encodes a gene product that performs a similar function in the organism. Orthologous genes are distinguished from homologous genes in that homologous genes share only sequence similarity and then often only in a portion of the sequence, which usually represents a functional domain such as a tyrosine kinase activity, a DNA binding domain, or the like. The degree of identity is a function of evolutionary separation and, in closely related species, the degree of identity can be 98 to 100%. The amino acid sequence of a protein encoded by an orthologous gene can be as little as 75% identical, but tends to be at least 80% identical, more preferably at least 90%, most preferably at least 95% identical to the amino acid sequence of the reference protein.

For finding orthologous genes, the probes are hybridized to nucleic acids from a species of interest under low stringency conditions and blots are then washed under conditions of increasing stringency. It is preferable that the wash stringency be such that sequences that are 85 to 100% identical will hybridize. More preferably, sequences 90 to 100% identical will hybridize and most preferably only sequences greater than 95% identical will hybridize. The low stringency condition is preferably one where sequences containing as much as 40-45% mismatches will be able to hybridize. This condition is established by Tm−40° C. to Tm−48° C. (see below). One of ordinary skill in the art will recognize that, due to degeneracy in the genetic code, amino acid sequences that are identical can be encoded by DNA sequences as little as 67% identical. Thus, it is preferable to make an overlapping series of shorter probes, on the order of 24 to 45 nucleotides, and individually hybridize them to the same arrayed library to avoid the problem of degeneracy introducing large numbers of mismatches. As evolutionary divergence increases, genome sequences also tend to diverge. Thus, one of skill will recognize that searches for orthologous genes between more divergent species will require the use of lower stringency conditions compared to searches between closely related species. Also, degeneracy is more of a problem for searches in the genome of a species more distant evolutionarily from the species that is the source of the SDF probe sequences.

Therefore the method described in Bouckaert et al., U.S. Patent Application Ser. No. 60/121,700, filed Feb. 25, 1999, herewith included by reference, can be applied to the SDFs of the present invention to isolate related genes from plant species which do not hybridize to the corn or *Arabidopsis* sequences of Table 2.

Identification of the relationship of nucleotide or amino acid sequences among plant species can be done by comparing the nucleotide or amino acid sequences of SDFs of the present application with nucleotide or amino acid sequences of other SDFs, such as those provided in any of the patent applications listed in U.S. Provisional Patent Application Ser. No. 60/145,088, all of which are expressly incorporated herein by reference.

The SDFs of the invention can also be used as probes to search for genes that are related to the SDF within a species. Such related genes are typically considered to be members of a "gene family." In such a case, the sequence similarity will often be concentrated into one or a few portions of the sequence. The portions of similar sequence that define the gene family typically encode a portion of a protein or RNA that has an enzymatic or structural function. The degree of identity in the amino acid sequence of the domain that defines the gene family is preferably at least 70%, more preferably 80 to 95%, most preferably 85 to 99%. To search for members of a gene family within a species, a "low stringency" hybridization is usually performed, but this will depend upon the size, distribution and degree of sequence divergence of domains that define the gene family. SDFs encompassing regulatory regions can be used to identify "coordinately expressed" genes by using the regulatory region portion of the SDF as a probe.

In the instances where the SDFs are identified as being expressed from genes that confer a particular phenotype, then the SDFs can also be used as probes to assay plants of different species for those phenotypes.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

I.C. Methods to Inhibit Gene Expression

C.1 Antisense

Polynucleotide SDFs in Table 2 represent, amongst others, sequences that are expressed in corn and/or *Arabidopsis*. Thus, the invention includes antisense constructs can be constructed based on these sequences to inhibit transcription and/or translation of said SDFs. To accomplish this, a polynucleotide segment from the desired gene is operably linked to a promoter such that the antisense strand of RNA will be transcribed.

The segment to be introduced generally will be substantially identical to at least a portion of the endogenous gene or genes to be repressed. The sequence, however, need not be perfectly identical to inhibit expression. Further, the antisense product may hybridize to the untranslated region instead of or in addition to the coding portion of the gene. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher sequence identity can be used to compensate for the use of a shorter sequence. Furthermore, the introduced sequence need not have the same intron or exon pattern, and homology of non coding segments may be equally effective. Normally, a sequence of between about 30 or 40 nucleotides and the full length of the transcript should be used, though a sequence of at least about 100 nucleotides is preferred, a sequence of at least about 200 nucleotides is more preferred, and a sequence of at least about 500 nucleotides is especially preferred.

C.2. Ribozymes

It is also contemplated that gene constructs representing ribozymes and based on the SDFs in Table 2 are an object of the invention. Ribozymes can also be used to inhibit expression of genes by suppressing the translation of the mRNA into a polypeptide. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs.

A number of classes of ribozymes have been identified. One class of ribozymes is derived from a number of small circular RNAs, which are capable of self cleavage and replication in plants. The RNAs replicate either alone (viroid RNAs) or with a helper virus (satellite RNAs). Examples include RNAs from avocado sunblotch viroid and the satellite RNAs from tobacco ringspot virus, luceme transient streak virus, velvet tobacco mottle virus, solanum nodiflorum mottle virus and subterranean clover mottle virus. The design and use of target RNA specific ribozymes is described in Haseloff et al. *Nature*, 334:585 (1988).

Like the antisense constructs above, the ribozyme sequence portion necessary for pairing need not be identical the target nucleotides to be cleaved, nor identical to the sequences in Table 2. Generally, the sequence in the ribozyme capable of binding to the target sequence exhibits substantial sequence identity a sequence in Table 2 or the complement thereof or to a portion of said sequence or complement. Further, the ribozyme sequence also need not be full length relative to either the primary transcription product or fully processed mRNA. The ribozyme can be equally effective in inhibiting mRNA translation by cleaving either in the untranslated or coding regions. Generally, higher sequence identity can be used to compensate for the use of a shorter sequence. Furthermore, the introduced sequence need not have the same intron or exon pattern, and homology of non-coding segments may be equally effective.

C.3. Sense Suppression

Another method of suppression is by introducing an exogenous copy of the gene to be suppressed. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279 (1990), and U.S. Pat. Nos. 5,034,323; 5,231,020; and 5,283,184. Generally, where inhibition of expression is desired, some transcription of the introduced sequence occurs. The effect may occur where the introduced sequence contains no coding sequence per se, but comprises only intron or untranslated sequences homologous to sequences present in the primary transcript of the endogenous sequence. The introduced sequence generally will be substantially identical to the endogenous sequence intended to be repressed. The minimal identity will typically be greater than about 65%, but a higher identity might exert a more effective repression of expression of the endogenous sequences. Sequence identity of more than about 80% is preferred, though about 95% to absolute identity would be most preferred. As with antisense regulation, the effect would likely apply to any other proteins within a similar family of genes exhibiting homology or substantial homology to the suppressing sequence.

C.4. Other Methods to Inhibit Gene Expression

Yet another means of suppressing gene expression is to insert a polynucleotide into the gene of interest to disrupt transcription or translation of the gene. Low frequency homologous recombination can be used to target a polynucleotide insert to a gene by flanking the polynucleotide insert with sequences that are substantially similar to the gene to be disrupted. Sequences from Table 2, fragments thereof, and substantially similar sequence thereto can be used for homologous recombination.

In addition, random insertion of polynucleotides into a host cell genome can also be used to disrupt the gene of interest. Azpiroz-Leehan et al., *Trends in Genetics* 13:152 (1997). In this method, screening for clones from a library containing random insertions is preferred to identifying those that have polynucleotides inserted into the gene of interest. Such screening can be performed using probes and/or primers described above based on sequences from Table 2, fragments thereof, and substantially similar sequence thereto. The screening can also be performed by selecting clones or R1 plants having a desired phenotype.

I.D. Methods of Functional Analysis

The constructs described in the methods under I.C. above can be used to determine the function of the polypeptide encoded by the gene that is targeted by the constructs.

Down regulating the transcription and translation of the targeted gene, the host cell or organisms, such as a plant, may produce phenotypic changes as compared to a wild-type cell or organism. In addition, in vitro assays can be used to determine if any biological activity, such as calcium flux, DNA transcription, nucleotide incorporation, etc., are being modulated by the down-regulation of the targeted gene.

I.E. Promoters

The SDFs of the invention are also useful as structural or regulatory sequences in a construct for modulating the expression of the corresponding gene in a plant or other organism, e.g. a symbiotic bacterium. For example, promoter sequences represented in Table 2 of a priority patent application can be useful in directing expression of coding sequences either as constitutive promoters or to direct expression in particular cell types, tissues, or organs or in response to environmental stimuli.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells and can be used to drive expression of a structural gene portion of an SDF. Such promoters need not be of plant origin. For example, promoters derived from plant viruses, such as the CaMV35S promoter or from *Agrobacterium tumefaciens* such as the T-DNA promoters, can be plant promoters. A typical example of constitutive promoter of plant origin is the promoter of the cowpea trypsin inhibitor gene. Typical examples of temporal and/or tissue specific promoters of plant origin that can be used with the polynucleotides of the present invention, are: PTA29, a promoter which is capable of driving gene expression specifically in tapetum and only during anther development (Koltonow et al., *Plant Cell,* 2:1201 (1990); RCc2 and RCc3, promoters that direct root-specific gene expression in rice (Xu et al., *Plant Mol. Biol.,* 27:237 (1995); TobRB27, a root-specific promoter from tobacco (Yamamoto et al., *Plant Cell,* 3:371 (1991)).

By "specific promoters" is meant promoters that have a high preference of driving gene expression in the specified tissue and/or at the specified time during the concerned tissue or organ development. By "high preference" is meant at least 3-fold, preferably 5-fold, more preferably at least 10-fold still more preferably at least 20-fold, 50-fold or 100-fold increase in expression in the desired tissue over the expression in any undesired tissue.

A typical example of an inducible promoter, which can be utilized with the polynucleotides of the present invention, is PARSK1, the promoter from the *Arabidopsis* gene encoding a serine-threonine kinase enzyme that is induced by dehydration, abscissic acid and sodium chloride (Wang and Goodman, *Plant J.* 8:37 (1995)).

With respect to the SDFs of the present invention a promoter is likely to be a relatively small portion of a genomic DNA (gDNA) sequence located in the first 2000 nucleotides upstream from an initial exon identified in a gDNA sequence or initial "ATG" or methionine codon in a corresponding cDNA or mRNA sequence. Such promoters are more likely to be found in the first 1000, most likely within the first 500 nucleotides upstream of an initial ATG or methionine codon of a cDNA sequence corresponding to a gDNA sequence. The portions of a particular gDNA sequence that function as a promoter in a plant cell will preferably be found to hybridize at medium or high stringency to gDNA sequences presented in Table 2 of any priority patent application.

Promoters are generally modular in nature. Short DNA sequences representing binding sites for proteins can be separated from each other by intervening sequences of varying length. For example, within a particular functional module protein binding sites may be constituted by regions of 5 to 60, preferably 10 to 30, more preferably 10 to 20 nucleotides. Within such binding sites, there are typically 2 to 6 nucleotides that specifically contact amino acids of the nucleic acid binding protein. The protein binding sites are usually separated from each other by 10 to several hundred nucleotides, typically by 15 to 150 nucleotides, often by 20 to 50 nucleotides. DNA binding sites in promoter elements often display dyad symmetry in their sequence. Often elements binding several different proteins, and/or a plurality of sites that bind the same protein, will be combined in a region of 100 to 1000 basepairs.

Elements that have transcription regulatory function can be isolated from their corresponding endogenous gene, or the desired sequence can be synthesized, and recombined in constructs to direct expression of a structural gene in a desired tissue-specific, temporal-specific or other desired manner of inducibility or suppression. When hybridizations are performed to identify or isolate elements of a promoter by hybridization to the long sequences presented in Table 2 of a priority patent application, conditions should be adjusted to account for the above-described nature of promoters. For example short probes, constituting the element sought, should be used under low temperature and/or high salt conditions. When long probes, which might include several promoter elements are used, low to medium stringency conditions are preferred when hybridizing to promoters across species.

Promoters can consist of a "basal promoter" that functions as a site for assembly of a transcription complex comprising an RNA polymerase, for example RNA polymerase II. A typical transcription complex will include additional factors such as TFIIB, TFIID, and TFIIE. Of these, TFIID appears to be the only one to bind DNA directly. Basal promoters frequently include a "TATA box" element usually located between 20 and 35 nucleotides upstream from the site of initiation of transcription. Basal promoters also sometimes include a "CCAAT box" element (typically a sequence CCAAT) and/or a GGGCG sequence, usually located between 40 and 200 nucleotides, preferably 60 to 120 nucleotides, upstream from the start site of transcription.

The promoter might also contain one or more "enhancers" and/or "suppressors" that function as binding sites for additional transcription factors that have the function of modulating the level of transcription with respect to tissue specificity of transcription, transcriptional responses to particular environmental or nutritional factors, and the like.

If a nucleotide sequence of the SDF, or part of said SDF, functions as a promoter or portion of a promoter, then nucleotide substitutions, insertions or deletions that do not substantially affect the binding of relevant DNA binding proteins would be considered equivalent to the exemplified nucleotide sequence. It is envisioned that there are instances where it is desirable to decrease the binding of relevant DNA binding proteins to "silence" or "down-regulate" a promoter, or conversely to increase the binding of relevant DNA binding proteins to "enhance" or "up-regulate" a promoter. In such instances, polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

I.F. UTRs and Junctions

Polynucleotides comprising untranslated (UTR) sequences and intron/exon junctions are also within the scope of the invention. UTR sequences include introns and 5' or 3' untranslated regions (5' UTRs or 3' UTRs). Portions of the sequences shown in Table 2 can comprise UTRs and introns or intron/exon junctions.

These portions of SDFs, especially UTRs, can have regulatory functions related to, for example, translation rate and mRNA stability. Thus, these portions of SDFs can be isolated for use as elements of gene constructs for expression of polynucleotides encoding desired polypeptides.

Introns of genomic DNA segments might also have regulatory functions. Sometimes promoter elements, especially transcription enhancer or suppressor elements, are found within introns. Also, elements related to stability of heteronuclear RNA and efficiency of transport to the cytoplasm for translation can be found in intron elements. Thus, these segments can also find use as elements of expression vectors intended for use to transform plants.

Just as with promoters, introns and UTR sequences and intron/exon junctions can vary from those shown in Table 2 of a priority patent application. Such changes from those sequences preferably will not affect the regulatory activity of the UTRs or intron or intron/exon junction sequences on expression, transcription, or translation. However, in some instances, down-regulation of such activity may be desired to modulate traits or phenotypic or in vitro activity.

I.G. Coding Sequences

Isolated polynucleotides of the invention can include coding sequences that encode polypeptides comprising an amino acid sequence encoded by the sequences in Table 2 or an amino acid sequence presented in Table 2.

A nucleotide sequence "encodes" a polypeptide if a cell (or a cell free in vitro system) expressing that nucleotide sequence produces a polypeptide having the recited amino acid sequence when the nucleotide sequence is transcribed and the primary transcript is subsequently processed and translated by a host cell (or a cell free in vitro system) harboring the nucleic acid. Thus, an isolated nucleic acid that "encodes" a particular amino acid sequence can be a genomic sequence comprising exons and introns or a cDNA sequence that represents the product of splicing thereof. An isolated nucleic acid "encoding an amino acid sequence" also encompasses heteronuclear RNA, which contains sequences that are spliced out during expression, and mRNA, which lacks those sequences.

Coding sequences can be constructed using chemical synthesis techniques or by isolating coding sequences or by modifying such synthesized or isolated coding sequences as described above.

In addition to encoding the polypeptide sequences of Table 2, which are native to corn or *Arabidopsis*, the isolated polynucleotides can be variant polynucleotides that encode mutants, fragments, and fusions of those native proteins. Such polypeptides are described below in part II.

In variant polynucleotides generally, the number of substitutions, deletions or insertions is preferably less than 20%, more preferably less than 15%; even more preferably less than 10%, 5%, 3% or 1% of the number of nucleotides comprising a particularly exemplified sequence. It is generally expected that non-degenerate nucleotide sequence changes that result in 1 to 10, more preferably 1 to 5 and most preferably 1 to 3 amino acid insertions, deletions or substitutions will not greatly affect the function of an encoded polypeptide. The most preferred embodiments are those wherein 1 to 20, preferably 1 to 10, most preferably 1 to 5 nucleotides are added to, deleted from and/or substituted in the sequences specifically disclosed in Table 2.

Insertions or deletions in polynucleotides intended to be used for encoding a polypeptide should preserve the reading frame. This consideration is not so important in instances when the polynucleotide is intended to be used as a hybridization probe.

II. Polypeptides

Polypeptides within the scope of the invention include both native proteins as well as mutants, fragments, and fusions thereof. Polypeptides of the invention are those encoded by any of the six reading frames of sequences shown in Table 2, preferably encoded by the three frames reading in the 5' to 3' direction of the sequences as shown.

Native polypeptides include the proteins encoded by the sequences shown in Table 2. Such native polypeptides include those encoded by allelic variants.

Variants, including mutants, will exhibit at least 80% sequence identity to those native polypeptides of Table 2. Sequence identity is used for polypeptides as defined above for polynucleotides. More preferably, the variants will exhibit at least 85% sequence identity; even more preferably, at least 90% sequence identity; more preferably at least 95%, 96%, 97%, 98%, or 99% sequence identity. "Fragments" of polypeptide or "portions" of polypeptides will exhibit similar degrees of identity to the relevant portions of the native polypeptide. Fusions will exhibit similar degrees of identity in that portion of the fusion represented by the variant of the native peptide.

Furthermore, variants will exhibit at least one of the functional properties of the native protein. Such properties include, without limitation, protein interaction, DNA interaction, biological activity, immunological activity, receptor binding, signal transduction, transcription activity, growth factor activity, secondary structure, three-dimensional structure, etc. As to properties related to in vitro or in vivo activities, the variants preferably exhibit at least 60% of the activity of the native protein; more preferably at least 70%, even more preferably at least 80%, 85%, 90% or 95% of at least one activity of the native protein.

A type of mutant of the native polypeptides comprises amino acid substitutions. "Conservative substitutions" are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Within the scope of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide. Amino acid substitutions may also be made in the sequences; conservative substitutions being preferred.

Antibodies

Isolated polypeptides can be utilized to produce antibodies. Polypeptides of the invention can generally be used, for example, as antigens for raising antibodies by known techniques. The resulting antibodies are useful as reagents for determining the distribution of the antigen protein within the tissues of a plant or within a cell of a plant. The antibodies are also useful for examining the expression level of proteins in various tissues, for example in a wild-type plant or following genetic manipulation of a plant, by methods such as Western blotting.

Antibodies of the present invention, both polyclonal and monoclonal, may be prepared by conventional methods. In general, the polypeptides of the invention are first used to immunize a suitable animal, such as a mouse, rat, rabbit, or goat. Rabbits and goats are preferred for the preparation of polyclonal sera due to the volume of serum obtainable, and the availability of labeled anti-rabbit and anti-goat antibodies as detection reagents. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera is obtained by bleeding the immunized animal into a glass or plastic container, incubating the blood at 25° C. for one hour, followed by incubating the blood at 4° C. for 2-18 hours. The serum is recovered by centrifugation (e.g., 1,000×g for 10 minutes). About 20-50 ml per bleed may be obtained from rabbits.

Monoclonal antibodies are prepared using the method of Kohler and Milstein, Nature 256: 495 (1975), or modification thereof. Typically, a mouse or rat is immunized as described above. However, rather than bleeding the animal to extract serum, the spleen (and optinally several large lymph nodes) is removed and dissociated into single cells. If desired, the spleen cells can be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected Mab-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by ther activity. For example, horseradish peroxidase is usually detected by its ability to convert 3,3',5,5'-tetramethylbenzidine (TNB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct modes. For example, $^{125}$I may serve as a radioactive label or as an electron-dense reagent. HRP may serve as an enzyme or as an antigen for a Mab. Further one may combine various labels for desired effect. For example, Mabs and avidin also require labels in the practice of this invention: thus, one might label a Mab with biotin, and detect its presence with avidin labeled with $^{125}$I, or with an anti-biotin Mab labeled with HRP. Other permutations and possibilities will be readily apparent to those of ordinary skill in the art, and are considered as equivalents within the scope of the instant invention.

In Vitro Applications of Polypeptides

Some polypeptides of the invention will have enzymatic activities that are useful in vitro. For example, the soybean trypsin inhibitor (Kunitz) family is one of the numerous families of proteinase inhibitors. It comprises plant proteins which have inhibitory activity against serine proteinases from the trypsin and subtilisin families, thiol proteinases and aspartic proteinases. Thus, these peptides find in vitro use in protein purification protocols and perhaps in therapeutic settings requiring topical application of protease inhibitors.

Delta-aminolevulinic acid dehydratase (EC 4.2.1.24) (ALAD) catalyzes the second step in the biosynthesis of heme, the condensation of two molecules of 5-aminolevulinate to form porphobilinogen. Thus, ALAD proteins can be used as catalysts in synthesis of heme derivatives. Enzymes of biosynthetic pathways generally can be used as catalysts for in vitro synthesis of the compounds representing products of the pathway.

II.A. Mutants, Fragments, and Fusions

Generally, mutants, fragments, or fusions of the polypeptides encoded by the maximum length seuqence (MLS) can exhibit at least one of the activities of the identified domains and/or related polypeptides described in Sections (C) and (D) of Table 1 corresponding to the MLS of interest.

II.A.(I) Mutants

A type of mutant of the native polypeptides comprises amino acid substitutions. "Conservative substitutions" are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Within the scope of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide. Amino acid substitutions may also be made in the sequences; conservative substitutions being preferred.

One preferred class of mutants are those that comprise (1) the domain of a MLS encoded polypeptide and/or (2) residues conserved between the MLS encoded polypeptide and related polypeptides of the MLS. For this class of mutants, the MLS encoded polypeptide sequence is changed by insertion, deletion, or substitution at positions flanking the domain and/or conserved residues.

Another class of mutants includes those that comprise a MLS encoded polypeptide sequence that is changed in the domain or conserved residues by a conservative substitution.

Yet another class of mutants includes those that lack one the in-vitro, in-vitro activities, or structural features of the MLS encoded polypeptides. One example is dominant negative mutants. Such mutant may comprises a MLS encoded polypeptide sequence with non-conservative changes in the domain or conserved residues.

II.A.(ii) Fragments

Fragments of particular interest are those that comprise the domain identified for the polypeptides encoded by MLS's of the instant invention and mutants thereof. Also, fragments that comprise a region of residues conserved between the MLS encoded polypeptides and its related polypeptides.

II.A.(iii) Fusions

Of interest are chimeras comprising (1) a fragment of the MLS encoded polypeptide or mutants thereof of interest and (2) a fragment of a polypeptide comprising the same domain. For example, an AP2 helix encoded by a MLS of the invention fused to second AP2 helix from ANT protein, which comprises two AP2 helices. The present invention also encompasses fusions of MLS encoded polypeptides, mutants, or fragments thereof fused with related proteins or fragments thereof.

Definition of Domains

The polypeptides of the invention may possess identifying domains as shown in Table 1. Domains are fingerprints or signatures that can be used to characterize protein families and/or motifs. Such fingerprints or signatures can comprise conserved (1) primary sequence, (2) secondary structure, and/or (3) three-dimensional conformation. Generally, each domain has been associated with either a family of proteins or a motif. Typically, these families and/or motifs have been correlated with specific in vitro and/or in vivo activities. The length of a domain can be any length, including the entirety of the sequence of a protein. Detailed descriptions of the domains, associated families and motifs, and correlated activities of the polypeptides of the instant invention are described below. Usually, the polypeptides with designated domain(s) can exhibit at least one activity that is exhibited by any polypeptides that comprises the same domain(s).

Specific domains within the MLS encoded polypeptides are indicated by the reference Table 1. In addition, the domains with the MLS encoded polypeptide can be defined by the region that exhibits at least 70% sequence identity with the consensus sequences listed in the detailed description below of each of the domains.

Except as otherwise noted, the protein domain descriptions given below are obtained from Prosite, (expasy.ch/prosite/) (contains 1030 documentation entries that describe 1366 different patterns, rules and profiles/matrices), and Pfam, (pfam.wustl.edu/browse.shtml).

Mov34 Family

Members of this family are found in proteasome regulatory subunits, eukaryotic initiation factor 3 (eIF3) subunits and regulators of transcription factors (Aravind L, Ponting CP, *Protein Sci.*, 7:1250-1254 (1998) and Hershey et al., *Biochimie*, 78:903-907 (1996)).

III. Methods of Modulating Polypeptide Production

Within the scope of invention are chimeric gene constructs wherein the promoter and the structural coding sequence and/or other regulatory sequences within said constructs are heterologous to each other. "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence originates from, are considered heterologous to said coding sequence. On the other hand, elements operatively linked in nature are not heterologous. Thus, the promoter and coding portion of a corn gene expressing an amino acid transporter are not heterologous to each other.

Such chimeric polynucleotides are of particular interest for modulating gene expression in a host cell upon transformation of said cell with said chimeric polynucleotide.

Also within the scope of the invention are DNA molecules, whereof at least a part or portion of these DNA molecules are presented in Table 2 of the present invention, and wherein the structural coding sequence is under the control of its own promoter and/or its own regulatory elements. Such DNA molecules are useful for transforming the genome of a host cell or an organism regenerated from said host cell.

Typically, such polynucleotides, whether chimeric or not, are "exogenous to" the genome of an individual host cell or the organism regenerated form said host cell, such as a plant cell, respectively for a plant, when initially or subsequently introduced into said host cell or organism, by any means other than by a sexual cross. Examples of means by which this can be accomplished are described below, and include *Agrobacterium*-mediated transformation (of dicots—e.g. Salomon et al. *EMBO J.*, 3:141 (1984); Herrera-Estrella et al., *EMBO J.*, 2:987 (1983); A. C. Vergunst et al., *Nucleic Acids Res.*, 26:11, 2729 (1998); of monocots, representative papers are those by Escudero et al., *Plant J.*, 10:355 (1996), Ishida et al., *Nature Biotechnology*, 14:745 (1996), May et al., *Bio/Technology*, 13:486 (1995)), biolistic methods (Armaleo et al., *Current Genetics*, 17:97 1990)), electroporation, in planta techniques, and the like. Such a plant containing the exogenous nucleic acid is referred to here as an R1 generation transgenic plant. Transgenic plants which arise from a sexual cross with another parent line or by selfing are "descendants or the progeny" of a $R_1$ plant and are generally called $F_n$ plants or $S_n$ plants, respectively, n meaning the number of generations.

The SDFs prepared as described herein can be used to prepare expression cassettes useful in a number of techniques for suppressing or enhancing expression.

III.A. Suppression

Expression cassettes of the invention can be used to suppress expression of endogenous genes which comprise the SDF sequence. Inhibiting expression can be useful, for instance, to tailor the ripening characteristics of a fruit (Oeller et al., *Science* 254:437 (1991)) or to influence seed size (WO98/07842) or to provoke cell ablation (Mariani et al., *Nature* 357: 384-387 (1992)).

As described above, a number of methods can be used to inhibit gene expression in plants, such as antisense, ribozyme, introduction of "exogenous" genes into a host cell, insertion of a polynucleotide sequence into the coding sequence and/or the promoter of the endogenous gene of interest, and the like.

III.A.1. Antisense

An expression cassette as described above can be transformed into a host cell or plant to produce an antisense strand of RNA. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805 (1988), and Hiatt et al., U.S. Pat. No. 4,801,340.

III.A.2. Ribozymes

Similarly, ribozyme constructs can be transformed into a plant to cleave mRNA and down-regulate translation.

III.A.3. Co-Suppression

Another method of suppression is by introducing an exogenous copy of the gene to be suppressed. Introduction of expression cassettes in which a nucleic acid is configured in the sense orientation with respect to the promoter has been shown to be an effective means by which to block the transcription of target genes. A detailed description of this method is described above.

III.A.4. Insertion of Sequences into the Gene to be Modulated

Yet another means of suppressing gene expression is to insert a polynucleotide into the gene of interest to disrupt transcription or translation of the gene. Homologous recombination can be used to target a polynucleotide insert to a gene by flanking the polynucleotide insert with sequences that are substantially similar to the gene to be disrupted. Sequences from Table 2, fragments thereof, and substantially similar sequence thereto can be used for homologous recombination.

In addition, random insertion of polynucleotides into a host cell genome can also be used to disrupt the gene of interest (Azpiroz-Leehan et al., *Trends in Genetics* 13:152 (1997)). In this method, screening for clones from a library containing random insertions is preferred for identifying those that have polynucleotides inserted into the gene of interest. Such screening can be performed using probes and/or primers described above based on sequences from Table 2, fragments thereof, and substantially similar sequence thereto. The screening can also be performed by selecting clones or R1 plants having a desired phenotype.

III.A.5. Promoter Modulation

Inactivation of the promoter that drives a gene of interest can modulate transcription and translation, and therefore expression. For example, triple helices can be formed using oligonucleotides based on sequences from Table 2, fragments thereof, and substantially similar sequence thereto. The oligonucleotide can be delivered to the host cell can bind to the promoter in the genome to form a triple helix and prevent transcription. Additionally, a vector capable of producing the oligonucleotide can be inserted into the host cell to deliver the oligonucleotide.

III.A.6. Expression of Mutants

An alternative method for inhibiting gene function is through the use of dominant negative mutants. These mutants will not exhibit an undesired activity of the native protein. Over-expression of these mutants can titrate out the undesired activity of the native protein. For example, the inactive mutant may bind to the same receptor as the native protein, preventing the native protein from activating a signal transduction pathway. Alternatively, the dominant-negative mutant can be an inactive enzyme still capable of binding to the same substrate as the native protein.

Dominant-negative mutants also can act upon the native protein itself to prevent activity. For example, the native protein may be active only as a homo-multimer or as one subunit of a hetero-multimer. Incorporation of an inactive subunit into the multimer with native subunit(s) can inhibit activity.

Thus, gene function can be modulated by insertion of an expression construct encoding a dominant-negative mutant into a host cell of interest.

III.B. Enhanced Expression

Enhanced expression of a gene of interest in a host cell can be accomplished by either (1) insertion of an exogenous gene; or (2) promoter modulation.

III.B.1. Insertion of an Exogenous Gene

Insertion of an expression construct encoding an exogenous gene can boost the number of gene copies expressed in a host cell.

Such expression constructs can comprise genes that either encode the native protein that is of interest or that encode a variant that exhibits enhanced activity as compared to the native protein. Such genes encoding proteins of interest can be constructed from the sequences from Table 2, fragments thereof, and substantially similar sequence thereto.

Such an exogenous gene can include either a constitutive promoter permitting expression in any cell in a host organism or a promoter that directs expression only in particular cells or times during a host cell life cycle or in response to environmental stimuli.

III.B.2. Promoter Modulation

Some promoters require binding of a regulatory protein to be activated. Other promoters may need a protein that signals a promoter binding protein to expose a polymerase binding site. In either case, over-expression of such proteins can be used to enhance expression of a gene of interest by increasing the activation time of the promoter.

Such regulatory proteins are encoded by some of the sequences in Table 2 of a priority patent application, fragments thereof, and substantially similar sequences thereto. Coding sequences for these proteins can be constructed as described above.

In some cases, duplication of enhancer elements or insertion of exogenous enhancer elements will increase expression of a desired gene from a particular promoter. The useful enhancer elements can be portions of one or more of the SDFs of Table 2 of a priority patent application.

III.C. Vector Construction

To use isolated SDFs of the present invention or a combination of them or parts and/or mutants and/or fusions of said SDFs in the above techniques, recombinant DNA vectors which comprise said SDFs and are suitable for transformation of cells, such as plant cells, are usually prepared.

Typically, a vector will comprise the exogenous gene, which in its turn comprises an SDF of the present invention to be introduced into the genome of a host cell, and which gene may be an antisense construct, a ribozyme construct, or a structural coding sequence with any desired transcriptional and/or translational regulatory sequences, such as promoters and 3' end termination sequences. Vectors of the invention can also include origins of replication, markers, homologous sequences, introns, etc.

A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for over-expression, a plant promoter fragment may be employed that will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1' or 2' promoter derived from T DNA of *Agrobacterium tumefaciens*, and other transcription initiation regions from various plant genes known to those of skill.

Alternatively, the plant promoter may direct expression of an SDF of the invention in a specific tissue (tissue specific promoters) or may be otherwise under more precise environmental control (inducible promoters). Examples of tissue specific promoters under developmental control include promoters that initiate transcription only in certain tissues, such as root, ovule, fruit, seeds, or flowers. The promoter from a LEC I gene, described in U.S. patent application Ser. No. 09/103,478, is particularly useful for directing gene expression so that a desired gene product is located in embryos or seeds. Other suitable promoters include those from genes encoding storage proteins or the lipid body membrane protein, oleosin. A few root-specific promoters are noted above. Examples of environmental conditions that may affect transcription by inducible promoters include anaerobic conditions, elevated temperature, or the presence of light. If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfooron or phosphinotricin.

IV.A. Coding Sequences

Generally, the sequence in the transformation vector and to be introduced into the genome of the host cell does not need to be absolutely identical to an SDF of the present invention. Also, it is not necessary for it to be full length, relative to either the primary transcription product or fully processed mRNA. Use of sequences shorter than full-length may be preferred to avoid concurrent production of some plants that are overexpressors. Furthermore, the introduced sequence need not have the same intron or exon pattern as a native gene. Also, heterologous non-coding segments can be incorporated into the coding sequence without changing the desired amino acid sequence of the polypeptide to be produced.

IV.B. Promoters

As explained above, introducing an exogenous SDF from the same species or an orthologous SDF from another species can modulate the expression of a native gene corresponding to that SDF of interest. Such an SDF construct can be under the control of either a constitutive promoter (e.g., the promoter of the 35S gene of the cauliflower mosaic virus or the promotor of the gene encoding the cowpea trypsin inhibitor) or a highly regulated inducible promoter (e.g., a copper inducible promoter). The promoter of interest can initially be either endogenous or heterologous to the species in question. When re-introduced into the genome of said species, such promoter becomes "exogenous" to said species. The promoter-SDF construct can be made using standard recombinant DNA techniques (Sambrook et al. 1989) and can be introduced to the species of interest by *Agrobacterium*-mediated transformation or by other means of transformation (e.g., particle gun bombardment) as referenced above. Over-expression of an SDF transgene can lead to co-suppression of the homologous gene thereby creating some alterations in the phenotypes of the transformed species as demonstrated by similar analysis of the chalcone synthase gene (Napoli et al., *Plant Cell*, 2:279 (1990) and van der Krol et al., *Plant Cell*, 2:291 (1990)). If an SDF is found to encode a protein with desirable characteristics, its over-expression can be controlled so that its accumulation can be manipulated in an organ- or tissue-specific manner utilizing a promoter having such specificity.

Likewise, if the promoter of an SDF (or an SDF that includes a promoter) is found to be tissue-specific or developmentally regulated, such a promoter can be utilized to drive the expression of a specific gene of interest (e.g., seed storage protein or root-specific protein). Thus, the level of accumulation of a particular protein can be manipulated or its spatial localization in an organ- or tissue-specific manner can be altered.

V. Transformation Techniques

A wide range of techniques for inserting exogenous polynucleotides are known for a number of host cells, including, without limitation, bacterial, yeast, mammalian, insect and plant cells.

Techniques for transforming a wide variety of higher plant species are well known and described in the technical and scientific literature. See, e.g. Weising et al., *Ann. Rev. Genet.*, 22:421 (1988); and Christou, Euphytica, v. 85, n.1-3:13-27, (1995).

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (Vergunst et al., *Nucl. Acids. Res.*, 26:2729 (1998) (site-directed integration using a Cre-Lox recombinase system); McCormac et al., *Mol. Biotechnol.*, 8:199 (1997); Hamilton, *Gene*, 200:107 (1997)); Salomon et al. *EMBO J.*, 3:141 (1984); Herrera-Estrella et al., *EMBO J.*, 2:987 (1983).

Microinjection techniques are known in the art and well described in the scientific and patent literature. The introduction of DNA constructs using polyethylene glycol precipitation is described in Paszkowski et al., *EMBO J.*, 3:2717 (1984). Electroporation techniques are described in Fromm et al., *Proc. Natl. Acad. Sci. USA*, 82:5824 (1985). Ballistic transformation techniques are described in Klein et al., *Nature*, 327:773 (1987). *Agrobacterium tumefaciens* mediated transformation techniques, including disarming and use of binary vectors, are well described in the scientific literature. See, for example Hamilton, C M., *Gene*, 200:107 (1997); Müller et al., *Mol. Gen. Genet.*, 207:171 (1987); Komari et al., *Plant J.*, 10:165 (1996); Venkateswarlu et al., *Biotechnology*, 9:1103 (1991) and Gleave, A P., *Plant Mol. Biol.*, 20:1203 (1992); Graves and Goldman, *Plant Mol. Biol.*, 7:34 (1986) and Gould et al., *Plant Physiology*, 95:426 (1991).

Transformed plant cells which are derived by any of the above transformation techniques can be cultured to regenerate a whole plant that possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture in "Handbook of Plant Cell Culture," pp. 124 176, MacMillan Publishing Company, New York, 1983; and Binding, Regeneration of Plants, Plant Protoplasts, pp. 21 73, CRC Press, Boca Raton, 1988. Regeneration can also be obtained from plant callus, explants, organs, or parts thereof. Such regeneration techniques are described generally in Klee et al., *Ann. Rev. of Plant Phys.*, 38:467 (1987). Regeneration of monocots (rice) is described by Hosoyama et al. (*Biosci. Biotechnol. Biochem.*, 58:1500 (1994)) and by Ghosh et al. (*J. Biotechnol.*, 32:1 (1994)). The nucleic acids of the invention can be used to confer desired traits on essentially any plant.

Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, V'tis, Vigna*, and, *Zea*.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The particular sequences of SDFs identified are provided in Table 2. One of ordinary skill in the art, having this data, can obtain cloned DNA fragments, synthetic DNA fragments or polypeptides constituting desired sequences by recombinant methodology known in the art or described herein.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in their entirety by such citation.

SEQUENCE LISTING

<160> NUMBER OF SEQ ID NOS: 4

<210> SEQ ID NO 1
<211> LENGTH: 1185

<210> SEQ ID NO 1
<211> LENGTH: 1185
<212> TYPE: DNA
<213> ORGANISM: Arabidopsis thaliana

<400> SEQUENCE: 1

```
aaacaaagaa aactgagaaa aaggttttct tataagatcc cattcttgta gcaaaaccc      60
agaagaacaa actttcgaag aagacgacta atcaattcat ctgattatgg agagactaca    120
gagaatcttc ggagctggtg gcggtttagg tcacgcatcg cctgattctc cgactctcga    180
tacatcggag caggtttaca tctcttctct cgctctcctc aagatgctta agcacggaag    240
agctggtgtt cctatggaag tcatgggatt gatgcttgga gagtttgtgg atgagtacac    300
tgttagggtt gtggatgttt ttgcgatgcc tcagagtggt actggtgtta gtgttgaagc    360
tgttgatcat gttttccaga ctaatatgct cgacatgctt aaacagaccg aagacctga    420
gatggtggtt ggttggtatc attcacatcc tggattcggc tgctggcttt ctggggttga    480
cattaatact caacagagtt ttgaagcttt gaatcagcga gctgtagcag tggtggtaga    540
tccgattcag agtgtgaaag gaaaggtggt gattgatgcg ttccgctcca taaatccaca    600
gaccattatg cttgggcacg aaccccgtca acaacatcg aaccttgggc acttgaacaa    660
accatcgatc caggctttga ttcacgggtt gaacagacac tattactcaa tagcaatcaa    720
ctataggaag aacagagcttg aggagaagat gttactcaac ctccacaaga gaaatggac    780
agatggtctg acgctaagac gctttgacac ccactccaag accaacgaac agacggtcca    840
ggagatgttg agcttggctg ctaaatataa caaggcggtt caagaggagg acgagttgtc    900
accagagaag ctggcaattg tgaatgtggg aagacaagat gcaaagaagc atctggaaga    960
acatgtctcg aacctcatgt catccaacat tgttcagaca ctaggcacta tgctcgacac   1020
tgttgtcttc tagagagctt acttctccag ccgcttcaag tcattgagct tgttcttct    1080
gcatctcttt ggcttctact gaatgttctc tttttatctg ctagcttttt acaaggttgt   1140
actgtactat gtgatttcgt tcgttaaggg cagggatcga tttcc                   1185
```

<210> SEQ ID NO 2
<211> LENGTH: 308
<212> TYPE: PRT
<213> ORGANISM: Arabidopsis thaliana

<400> SEQUENCE: 2

```
Met Glu Arg Leu Gln Arg Ile Phe Gly Ala Gly Gly Leu Gly His
  1               5                  10                  15

Ala Ser Pro Asp Ser Pro Thr Leu Asp Thr Ser Glu Gln Val Tyr Ile
                 20                  25                  30

Ser Ser Leu Ala Leu Leu Lys Met Leu Lys His Gly Arg Ala Gly Val
             35                  40                  45

Pro Met Glu Val Met Gly Leu Met Leu Gly Glu Phe Val Asp Glu Tyr
         50                  55                  60

Thr Val Arg Val Val Asp Val Phe Ala Met Pro Gln Ser Gly Thr Gly
 65                  70                  75                  80

Val Ser Val Glu Ala Val Asp His Val Phe Gln Thr Asn Met Leu Asp
                 85                  90                  95

Met Leu Lys Gln Thr Gly Arg Pro Glu Met Val Val Gly Trp Tyr His
            100                 105                 110

Ser His Pro Gly Phe Gly Cys Trp Leu Ser Gly Val Asp Ile Asn Thr
        115                 120                 125

Gln Gln Ser Phe Glu Ala Leu Asn Gln Arg Ala Val Ala Val Val
    130                 135                 140
```

```
Asp Pro Ile Gln Ser Val Lys Gly Lys Val Ile Asp Ala Phe Arg
145                 150                 155                 160

Ser Ile Asn Pro Gln Thr Ile Met Leu Gly His Glu Pro Arg Gln Thr
                165                 170                 175

Thr Ser Asn Leu Gly His Leu Asn Lys Pro Ser Ile Gln Ala Leu Ile
            180                 185                 190

His Gly Leu Asn Arg His Tyr Tyr Ser Ile Ala Ile Asn Tyr Arg Lys
        195                 200                 205

Asn Glu Leu Glu Glu Lys Met Leu Leu Asn Leu His Lys Lys Lys Trp
    210                 215                 220

Thr Asp Gly Leu Thr Leu Arg Arg Phe Asp Thr His Ser Lys Thr Asn
225                 230                 235                 240

Glu Gln Thr Val Gln Glu Met Leu Ser Leu Ala Ala Lys Tyr Asn Lys
                245                 250                 255

Ala Val Gln Glu Glu Asp Glu Leu Ser Pro Glu Lys Leu Ala Ile Val
            260                 265                 270

Asn Val Gly Arg Gln Asp Ala Lys Lys His Leu Glu Glu His Val Ser
        275                 280                 285

Asn Leu Met Ser Ser Asn Ile Val Gln Thr Leu Gly Thr Met Leu Asp
    290                 295                 300

Thr Val Val Phe
305

<210> SEQ ID NO 3
<211> LENGTH: 269
<212> TYPE: PRT
<213> ORGANISM: Arabidopsis thaliana

<400> SEQUENCE: 3

Met Leu Lys His Gly Arg Ala Gly Val Pro Met Glu Val Met Gly Leu
1               5                   10                  15

Met Leu Gly Glu Phe Val Asp Glu Tyr Thr Val Arg Val Val Asp Val
                20                  25                  30

Phe Ala Met Pro Gln Ser Gly Thr Gly Val Ser Val Glu Ala Val Asp
            35                  40                  45

His Val Phe Gln Thr Asn Met Leu Asp Met Leu Lys Gln Thr Gly Arg
        50                  55                  60

Pro Glu Met Val Val Gly Trp Tyr His Ser His Pro Gly Phe Gly Cys
65                  70                  75                  80

Trp Leu Ser Gly Val Asp Ile Asn Thr Gln Gln Ser Phe Glu Ala Leu
                85                  90                  95

Asn Gln Arg Ala Val Ala Val Val Asp Pro Ile Gln Ser Val Lys
            100                 105                 110

Gly Lys Val Val Ile Asp Ala Phe Arg Ser Ile Asn Pro Gln Thr Ile
        115                 120                 125

Met Leu Gly His Glu Pro Arg Gln Thr Thr Ser Asn Leu Gly His Leu
    130                 135                 140

Asn Lys Pro Ser Ile Gln Ala Leu Ile His Gly Leu Asn Arg His Tyr
145                 150                 155                 160

Tyr Ser Ile Ala Ile Asn Tyr Arg Lys Asn Glu Leu Glu Glu Lys Met
                165                 170                 175

Leu Leu Asn Leu His Lys Lys Lys Trp Thr Asp Gly Leu Thr Leu Arg
            180                 185                 190

Arg Phe Asp Thr His Ser Lys Thr Asn Glu Gln Thr Val Gln Glu Met
```

-continued

```
            195                 200                 205
Leu Ser Leu Ala Ala Lys Tyr Asn Lys Ala Val Gln Glu Glu Asp Glu
        210                 215                 220

Leu Ser Pro Glu Lys Leu Ala Ile Val Asn Val Gly Arg Gln Asp Ala
225                 230                 235                 240

Lys Lys His Leu Glu Glu His Val Ser Asn Leu Met Ser Ser Asn Ile
                245                 250                 255

Val Gln Thr Leu Gly Thr Met Leu Asp Thr Val Val Phe
            260                 265

<210> SEQ ID NO 4
<211> LENGTH: 259
<212> TYPE: PRT
<213> ORGANISM: Arabidopsis thaliana

<400> SEQUENCE: 4

Met Glu Val Met Gly Leu Met Leu Gly Glu Phe Val Asp Glu Tyr Thr
  1               5                  10                  15

Val Arg Val Val Asp Val Phe Ala Met Pro Gln Ser Gly Thr Gly Val
                 20                  25                  30

Ser Val Glu Ala Val Asp His Val Phe Gln Thr Asn Met Leu Asp Met
             35                  40                  45

Leu Lys Gln Thr Gly Arg Pro Glu Met Val Val Gly Trp Tyr His Ser
     50                  55                  60

His Pro Gly Phe Gly Cys Trp Leu Ser Gly Val Asp Ile Asn Thr Gln
 65                  70                  75                  80

Gln Ser Phe Glu Ala Leu Asn Gln Arg Ala Val Ala Val Val Val Asp
                 85                  90                  95

Pro Ile Gln Ser Val Lys Gly Lys Val Val Ile Asp Ala Phe Arg Ser
                100                 105                 110

Ile Asn Pro Gln Thr Ile Met Leu Gly His Glu Pro Arg Gln Thr Thr
            115                 120                 125

Ser Asn Leu Gly His Leu Asn Lys Pro Ser Ile Gln Ala Leu Ile His
    130                 135                 140

Gly Leu Asn Arg His Tyr Tyr Ser Ile Ala Ile Asn Tyr Arg Lys Asn
145                 150                 155                 160

Glu Leu Glu Glu Lys Met Leu Leu Asn Leu His Lys Lys Lys Trp Thr
                165                 170                 175

Asp Gly Leu Thr Leu Arg Arg Phe Asp Thr His Ser Lys Thr Asn Glu
            180                 185                 190

Gln Thr Val Gln Glu Met Leu Ser Leu Ala Ala Lys Tyr Asn Lys Ala
        195                 200                 205

Val Gln Glu Glu Asp Glu Leu Ser Pro Glu Lys Leu Ala Ile Val Asn
    210                 215                 220

Val Gly Arg Gln Asp Ala Lys Lys His Leu Glu Glu His Val Ser Asn
225                 230                 235                 240

Leu Met Ser Ser Asn Ile Val Gln Thr Leu Gly Thr Met Leu Asp Thr
                245                 250                 255

Val Val Phe
```

What is claimed is:

1. An isolated polynucleotide having a nucleic acid sequence that encodes a polypeptide having MOV34 family activity, wherein said polypeptide comprises an amino acid sequence with at least 95 percent identity to the sequence set forth in SEQ ID NO:2.

* * * * *

UNITED STATES PATENT AND TRADEMARK OFFICE
CERTIFICATE OF CORRECTION

PATENT NO.         : 7,479,555 B2
APPLICATION NO.    : 11/180418
DATED              : January 20, 2009
INVENTOR(S)        : Nickolai Alexandrov Page 1 of 1

It is certified that error appears in the above-identified patent and that said Letters Patent is hereby corrected as shown below:

Title Page Item (63), Related U.S. Application Data, after "Jul. 21, 2000", please insert --abandoned--;

Column 1, line 16, please delete "Jul," and insert --Jul.-- therefor;

Column 1, line 16, after "2000" please insert --abandoned--.

Signed and Sealed this

Eleventh Day of August, 2009

David J. Kappos
*Director of the United States Patent and Trademark Office*